United States Patent [19]

Meador et al.

[11] Patent Number: 5,411,065
[45] Date of Patent: May 2, 1995

[54] LIQUID SPECIMEN TRANSFER APPARATUS AND METHOD

[75] Inventors: James W. Meador; Thomas G. Miller; Christopher T. Nikirk, all of Houston; Louis A. Waters, Jr., Bellaire; Sean M. Donnelly, Houston, all of Tex.

[73] Assignee: KVM Technologies, Inc., Houston, Tex.

[21] Appl. No.: 179,436

[22] Filed: Jan. 10, 1994

[51] Int. Cl.[6] ............................ B65B 1/04; B65B 3/04
[52] U.S. Cl. .......................................... 141/1; 141/26; 141/98; 141/114; 141/130; 422/63; 436/180; 73/863.84
[58] Field of Search .................. 141/1, 25, 26, 27, 81, 141/98, 114, 117, 130; 422/63; 436/180; 222/214, 81, 82, 152; 73/863.81, 863.83, 863.84

[56] References Cited

U.S. PATENT DOCUMENTS

| | | | |
|---|---|---|---|
| 4,609,017 | 9/1986 | Coulter et al. | 141/1 |
| 5,069,364 | 12/1991 | McGill | 222/214 |
| 5,174,961 | 12/1992 | Smith | 422/63 |
| 5,238,031 | 8/1993 | Baeumer et al. | 141/27 |
| 5,265,655 | 11/1993 | Hirsch | 141/130 |

Primary Examiner—Henry J. Recla
Assistant Examiner—Steven O. Douglas
Attorney, Agent, or Firm—Tim L. Burgess

[57] ABSTRACT

A method of obtaining aliquots or samples from a liquid specimen collection container and an apparatus which automateally perforths those methods involves transferring a sample of liquid from a sealed non-deformingly expandable container containing gas and the liquid without contaminating the liquid remaining inside the container, and comprises (a) non-deformingly volumetrically expanding the sealed container sufficiently to reduce pressure therein below ambient pressure outside the container, (b) applying heat selectively to a locus on said enlarged container to non-invasively create a hole having a diameter effective to equilibrate the pressure inside the container with said ambient pressure without loss of liquid from the container, and (c) non-deformingly volumetrically reducing the container to expel liquid from the container through the hole.

36 Claims, 22 Drawing Sheets

LIQUID SPECIMEN TRANSFER APPARATUS AND METHOD

FIELD OF THE INVENTION

The present invention relates generally to the field of fluid sampling and testing and most particularly to urine specimen collection devices and apparatus for processing for substance abuse testing.

BACKGROUND OF THE INVENTION

In fields such as clinical medicine, forensic sciences, environmental quality testing, food quality assurance, drug testing, and other areas, it has become possible to determine the presence and/or amount of trace substances in test samples even when such substances are present in very low concentrations (on the order of parts per million, or even billion). For example, in clinical testing, medical procedures, the consequences of which even if favorable can alter family life, rest on veracity of identification and non-adulteration of a test specimen. Substance abuse has given rise to widespread urine specimen testing. Positive test results identifying an illicit substance in a specimen may have a profound impact on the donor's career or employment. In the proper circumstances, positive test results may also result in criminal liability for the donor. As another example, the U.S. Environmental Protection Agency conducts a variety of ongoing testing programs. These testing programs are intended to guarantee compliance with standards for maximum levels of toxic and/or radioactively contaminated fluids, such as plant effluent, and results of tests can figure in civil and criminal liabities.

The familial, societal and juridical consequences which ride on the trustworthiness of test results and absolute linkage of test results to the specimen actually collected dictate the need for methods and apparatus that provide:

(1) honest specimens;
(2) specimen collection containers that are
   (a) tamper proof, and
   (b) capable of providing
      (i) multiple sampling from the specimen container to obtain aliquots of
         (x) a first sample on which to conduct a screening test, and
         (y) a subsequent sample, if the first sample screens positive, on which to conduct rigorous verification testing, and
      (ii) a redundant previously unsampled original specimen for third party confirmation testing of results obtained in the screening and verification tests;
(3) operations for obtaining multiple aliquots from specimen containers which
   (a) eliminate potential sources for adulteration of the specimen from which the aliquot is taken, and
   (b) eliminate potential sources of adulteration of the aliquot taken from the specimen container;
(4) custody and identification tracing procedures that assure certainty of specimen identity ("chain of custody") during every phase of
   (a) specimen collection, then
   (b) obtaining aliquots from specimen containers, then
   (c) the sequences of
      (i) screening tests, then
      (ii) subsequent verification testing of positive screens, and then
      (iii) third party testing to confirm positive analyses of screen positives, and
   (d) storage of specimen at the testing facility,
(5) safeguards from dishonest intervention for the purpose of defeating honest testing operations.

Particularly in the area of testing for substance abuse, large and increasingly high volumes of urine testing has created a need for specialized specimen collection containers and automated handling of specimen collection containers.

Thus, there has been a need for a liquid specimen collection containers that provide for more than one isolated specimen of a sample to provide redundancy for third party confirmation testing, that automatically retains an archival specimen so that tests may be repeated on the identical specimen and the results of the screening tests either verified or disproved, and that cannot be accessed without evident tamper. Providing these benefits, a specimen collection container device has been invented which eliminates human contact with the specimen once the specimen is sealed in the device, and which provides split specimen collection. This device is described in pending U.S. Patent application Ser. No. 08/027,860, filed Mar. 8, 1993, now abandoned, and entitled "Fluid Sample Receptacle", and also described briefly herein.

A need exists for automated sampling to obtain aliquots from of specimen collection devices that have certain features of devices described in U.S. Patent application Ser. No. 08/027,860 and herein. The aliquots are used for the screening and verification tests. Automated sampling must, however, assure or contribute to the assurance of the objectives set forth above for operations for obtaining multiple aliquots from specimen containers, for custody and identification tracing procedures that assure certainty of specimen identity ("chain of custody") during operations for obtaining aliquots from specimen containers and linkage to specimen storage, and for safeguards from dishonest intervention for the purpose of defeating honest testing operations.

SUMMARY OF THE INVENTION

These and other objectives are provided by this invention, which comprises a method of obtaining aliquots or samples from a liquid specimen collection container and provides an apparatus which automatedly performs those methods.

The method involves transferring a sample of liquid from a sealed non-deformingly expandable container containing gas and the liquid without contaminating the liquid remaining inside the container, and comprises (a) non-deformingly volumetrically expanding said sealed container sufficiently to reduce pressure therein below ambient pressure outside the container, (b) applying heat selectively to a locus on said enlarged container to non-invasively create a hole having a diameter effective to equilibrate the pressure inside the container with said ambient pressure without loss of liquid from the container, and (c) non-deformingly volumetrically reducing said container to expel liquid from the container through said hole. More narrowly, the method has the locus at a bottom portion of the container when the hole is being created, and step (b) includes creating said hole with a laser beam or with a heated gas stream column. In a particular, the hole has a diameter effective in said enlarged container to provide surface tension at the hole greater than the hydrostatic pressure within the enlarged container.

By non-invasively creating the hole in the nozzle closure, the integrity of the specimen inside the container is preserved.

By expanding the sealed container to reduce pressure in it below ambient pressure before opening the nozzle closure, specimen is not expelled upon opening from the chamber onto apparatus employed in the transfer of aliquot samples of specimen from the container, helping eliminate contamination and adulteration of other specimen samples from contaminated apparatus.

By creating a hole in the nozzle closure of diameter effective to prevent loss of liquid from the container, liquid is kept in the container even though the nozzle is at the bottom of the container. This helps eliminate contamination and adulteration of other specimen samples from contaminated apparatus.

The invention includes methods of tracking the identity of a container, a specimen aliquot taken from the container, and the location of the sampled container in a rack which suitably is used for storage of the container.

The invention includes apparatus which carries out the methods. The apparatus includes elements and assemblages of elements for transferring to a receptacle an aliquot of an aqueous liquid specimen from a sealed non-deformingly expandable container containing gas and a liquid.

In its broadest sense, the apparatus comprises means for non-deformingly volumetrically expanding and constricting the sealed container to vary volume therein, upon expansion to reduce pressure therein below ambient pressure outside the container, and upon constriction to expel liquid from the container through a hole formed in the duct closure, and means for applying heat selectively to a locus on the duct closure to non-invasively create a hole in the closure having a diameter effective to equilibrate the pressure inside the theretofore sealed container with the ambient pressure without loss of liquid from the container and for applying heat selectively to the periphery of the locus of the container after constriction thereof to melt close the hole.

The container on which the apparatus operates preferably has a bottom portion including at least one nozzle portion dependent therefrom, the nozzle having a duct opening into the container and a closure closing the duct remotely from the duct opening. The container preferably has a readable identification code on the exterior thereof and is one of a plurality of containers in a rack. The rack preferably has a readable identification code and includes a code structure adjacent each container for identification of the location of the container in the rack. The receptacle preferably has a readable identification code on the exterior thereof and is one of a plurality of receptacles in a holder.

The apparatus of this invention in a more narrow aspect of the invention includes (a) means for feeding a first the holder for advancement in a first direction to place a first receptacle below a dispense station; (b) means for reading the code of the first receptacle; (c) means for reading the rack code identification to provide a signal for use for correlating the code identification of the rack to the code identification of the receptacle in the holder; (d) means for feeding a first rack in a second direction transverse to the first direction to place the first container at the dispense station above the first receptacle; (e) means for reading the code of the first container for correlating the code identification of the container at the dispense station to the code identification of the first receptacle below the dispense station; (f) means for sensing and determining the position of a container nozzle at the dispense station; (g) means for rotating the first container past the means for reading the code of the container and past the means for sensing the position of a the nozzle, for rotating the container at the dispensing station to position the nozzle at a nozzle opening position, for rotating the first container at the dispensing station to position the nozzle above the first receptacle, and for rotating the first container at the dispensing station to position the nozzle at a nozzle hole closing position; (h) means for non-deformingly volumetrically expanding and constricting the sealed container to vary volume therein, upon expansion to reduce pressure therein below ambient pressure outside the container, and upon constriction to expel liquid from the container through a hole formed in the duct closure; (i) means for applying heat selectively to a locus on the duct closure to non-invasively create a hole in closure having a diameter effective to equilibrate the pressure inside the theretofore sealed container with the ambient pressure without loss of liquid from the container and for applying heat selectively to the periphery of the locus to melt close the hole; and (j) means for elevating the first receptacle from the holder so that the bottom of the nozzle is below the top of the receptacle and for lowering the first receptacle to the holder so that the bottom of the nozzle is above the top of the receptacle.

A preferred embodiment of apparatus for conducting the methods of this invention is described below in connection with the drawings. The invention claimed is not limited to the specific structure described below nor its specific operation, but includes substantially equivalent ways of performing the same functions to accomplish the same results as described and claimed.

DESCRIPTION OF THE DRAWINGS

FIG. 4b is a side sectional view of a partially assembled specimen collection container of FIG. 4a.

FIG. 4c is a side sectional view of an assembled specimen collection container of FIG. 4a.

FIG. 4d is a side perspective view of an assembled specimen collection container of FIG. 4a.

FIG. 5b is a bottom plan view of the modified primary collection chamber bellows assembly of FIG. 5a.

FIG. 5c is a side sectional view of the modified primary collection chamber bellows assembly of FIG. 5a.

FIG. 5d is a bottom perspective view of the modified primary collection chamber bellows assembly device of FIG. 5a.

FIG. 5e is a top perspective view of the modified primary collection chamber bellows assembly device of FIG. 5a.

FIG. 13b is a side sectional view of the container manipulation device of FIG. 13a.

FIG. 16b is a partially side sectional view of the manipulation systems for a liquid specimen container and aliquot receptacle shown in FIG. 16a.

FIG. 16c is a top plan view of the manipulation systems for a liquid specimen container and aliquot receptacle shown in FIG. 16a.

DESCRIPTION OF THE PREFERRED EMBODIMENT

Machine Orientation

Figure 1:
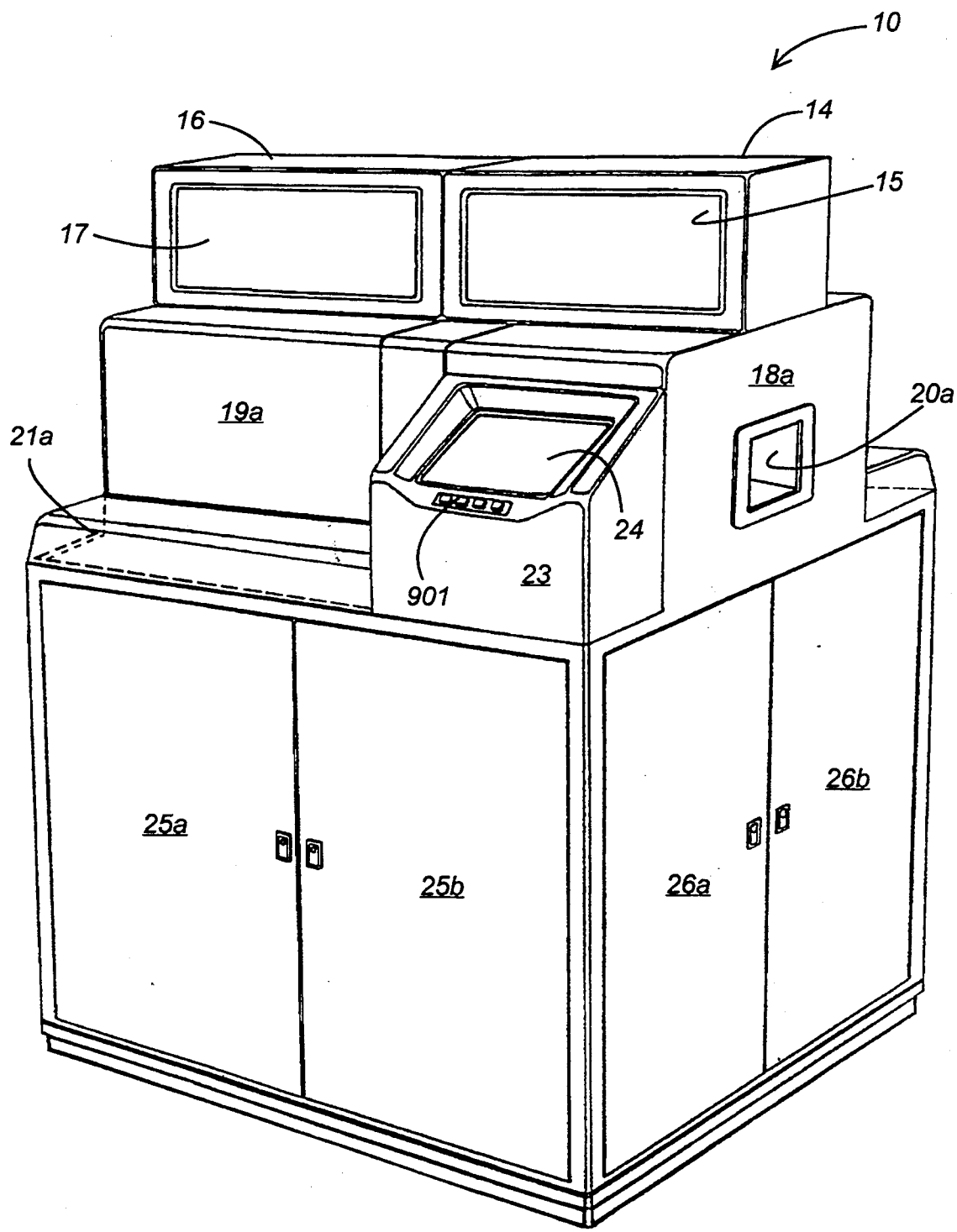
FIG. 1 is a from perspective view of an automated liquid specimen transfer apparatus.
Figure 2:
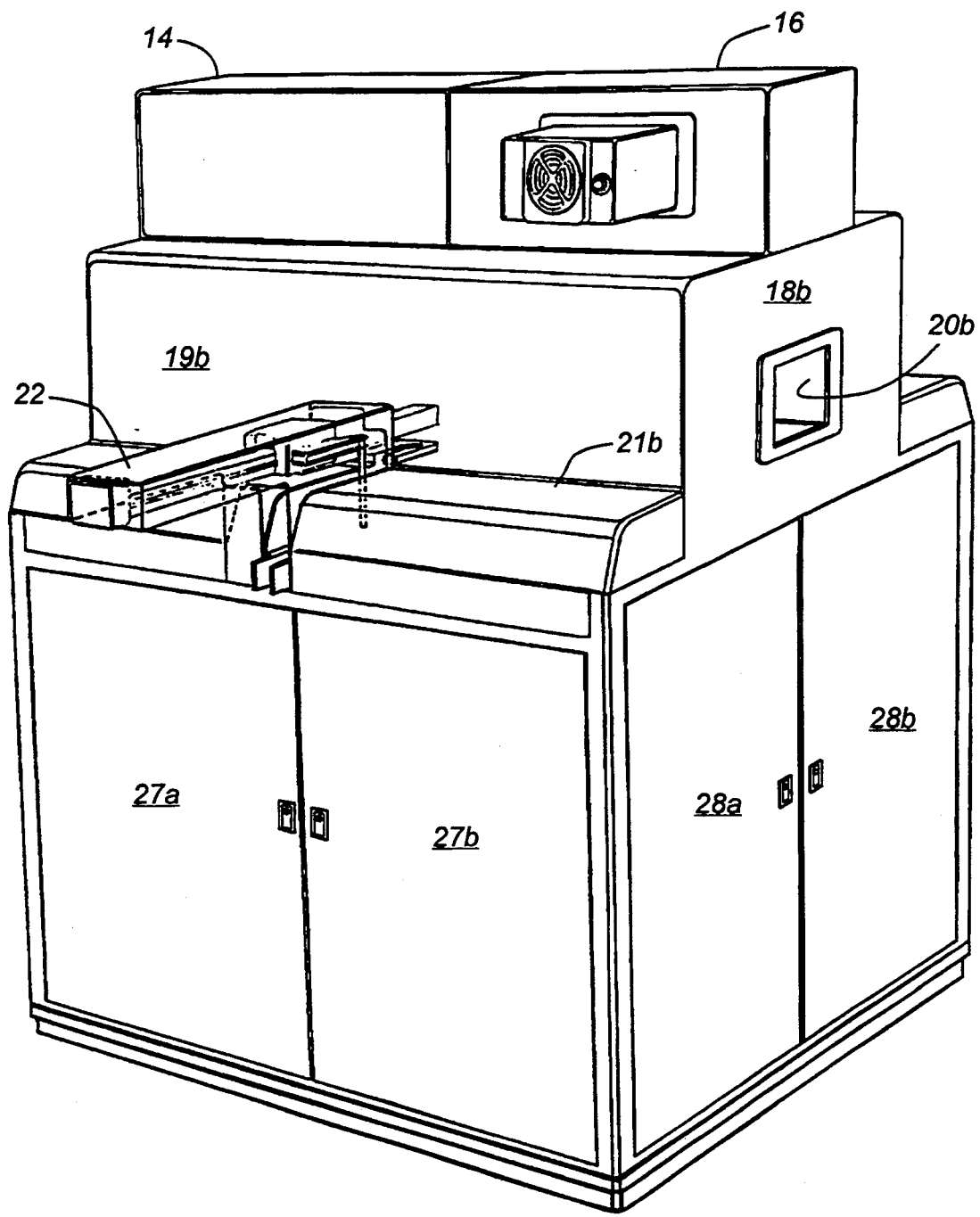
FIG. 2 is a rear perspective view of the automated liquid specimen transfer apparatus shown in FIG. 1.
Figure 3:
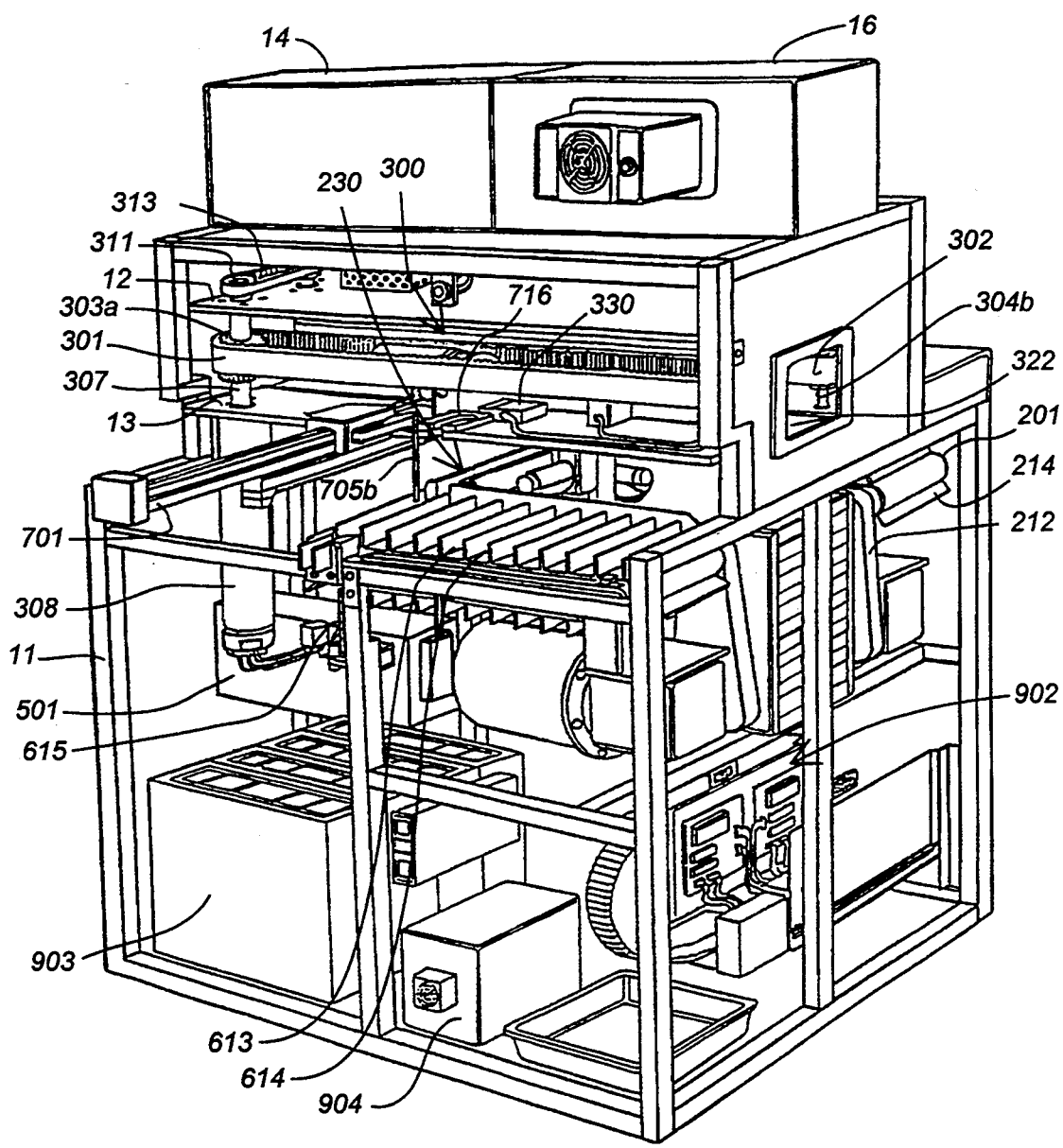
FIG. 3 is a rear perspective view of the automated liquid specimen transfer apparatus shown in FIG. 2, with panel covers removed.

Referring to FIGS. 1-3, reference numeral 10 indicates an automated liquid specimen transfer apparatus or machine in accordance with the present invention. Referring to FIG. 1 for orientation, the view is from the front, and "right" is to the right side of apparatus 10 as viewed from the front. In FIGS. 2 and 3, a view from the rear, the right side of the apparatus is to the reader's left. Referring particularly to FIG. 3, apparatus 10 includes a support structure comprising a framework 11, support plates attached to the framework, including upper plate 12 and lower plate 13, and referring to FIGS. 1–2, also comprises panels, covers and doors covering the framework. At the top of the machine are top right panel group 14 and windowed door 15, which provide an upper right cabinet that houses pumps for controls and blinds system 800. Also at the top are top left panel group 16 and windowed door 17, which provide an upper left cabinet for bottles for controls and blinds system 800. In an intermediate portion of the machine are intermediate right and left panels 18a and 18b respectively and front and rear panels 19a and 19b respectively that cover a portion of the machine containing specimen container and aliquot receptacle processing systems 225, 300, 400, 450 and 500 hereinafter described. Panel 18a surrounds an entrance portal 20a to specimen container rack track 300. Panel 18b surrounds an exit portal 20b to specimen container rack track 300. Cover 21a covers an aliquot receptacle holder input queue system 100 hereinafter described. Cover 21b (see also FIG. 11) covers an aliquot receptacle holder output queue system 600 hereinafter described. Cover 22 covers an aliquot output off machine transfer system 700 hereinafter described. Panel group 23 covers a computer monitor 24 cooperative with the machine computer system. The lower portion of the machine has front doors 25a, 25b, right side doors 26a, 26b, rear doors 27a, 27b and left side doors 28a, 28b. These doors with the adjacent lower portion panels provide a lower cabinet portion in the support structure. This lower cabinet portion houses controllers (generally indicated by reference numeral 903), power supply (generally indicated by reference numeral 2), machine computer systems (generally indicated by reference numeral 902), relays, sensors, motors, drives, a laser system housing 501 and other systems hereinafter described.

Apparatus 10 functions to transfer a liquid specimen from a liquid specimen container comprising a closed chamber to a receptacle which will be off loaded from apparatus 10 to another machine for analytical testing. In order that the arrangement of elements and operation of apparatus 10 is more conveniently described, a liquid specimen container suitable for use in apparatus 10 is preliminarily described. After the container is described, a rack is described for holding a plurality of the containers for handling by apparatus 10. Then a receptacle system for receipt of an aliquot of liquid specimen from a container is described in conjunction with a holder device for aliquot receptacles.

Liquid Specimen Container

Figure 4A:
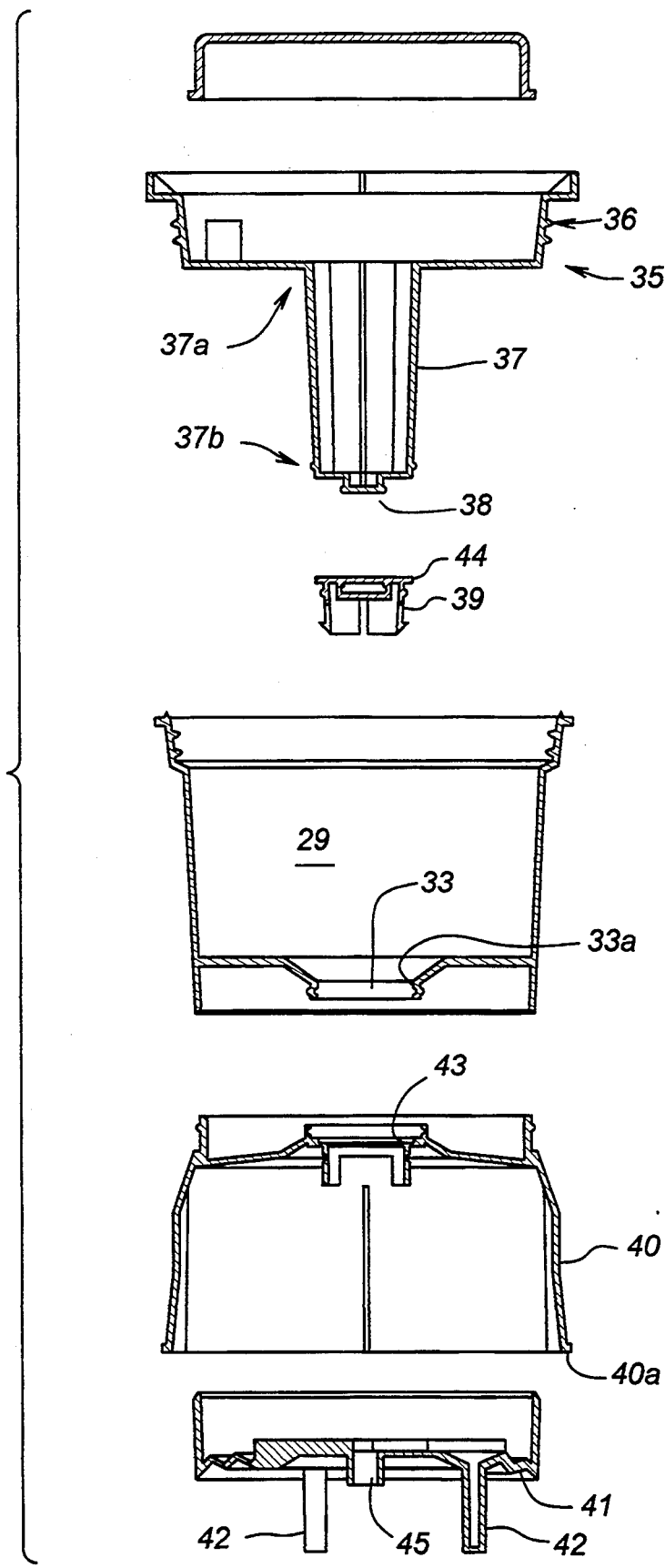
FIG. 4a is an exploded side sectional view of a specimen collection container suitable for use in an apparatus of the present invention.
Figures 4B, 4C:
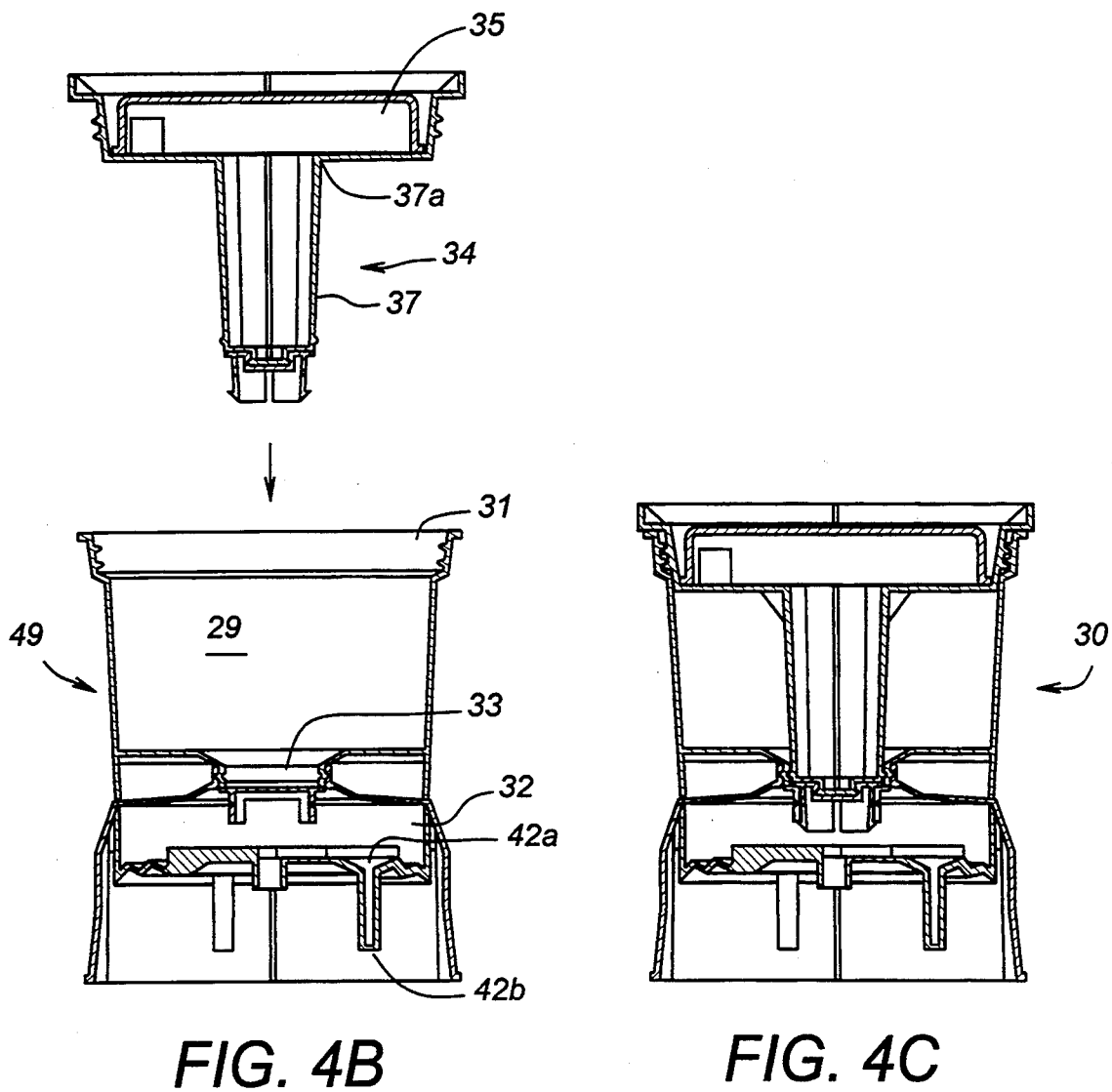
Figure 4D:
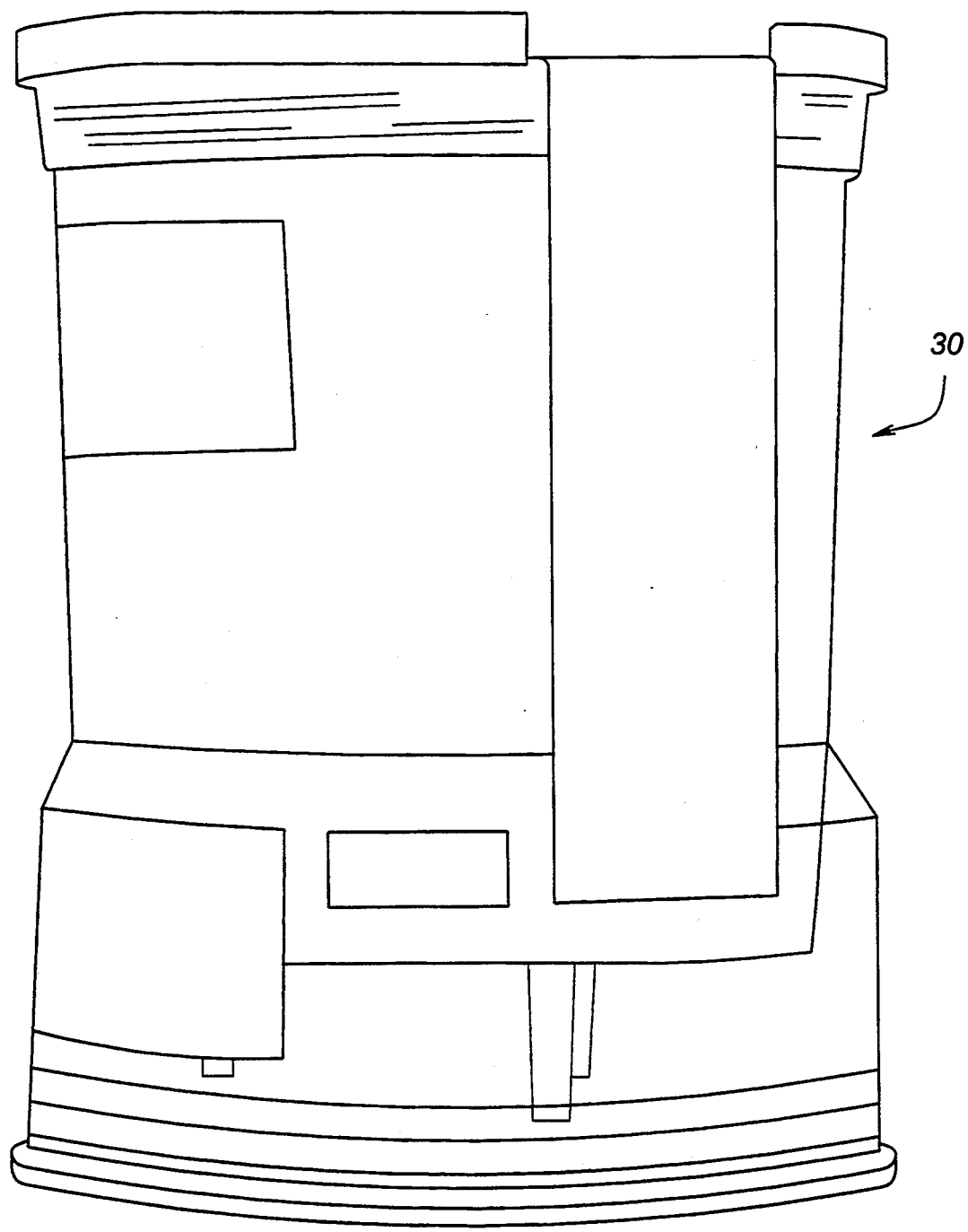
Figure 5A:
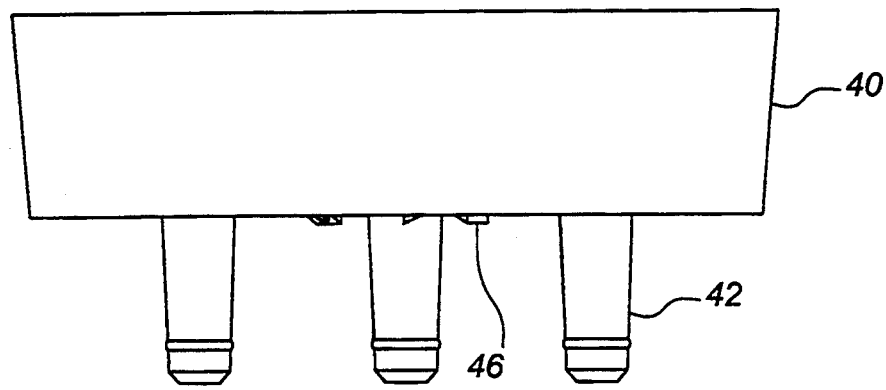
FIG. 5a is side elevational view of a modified primary collection chamber bellows assembly of the specimen collection container of FIG. 4.
Figure 5B:
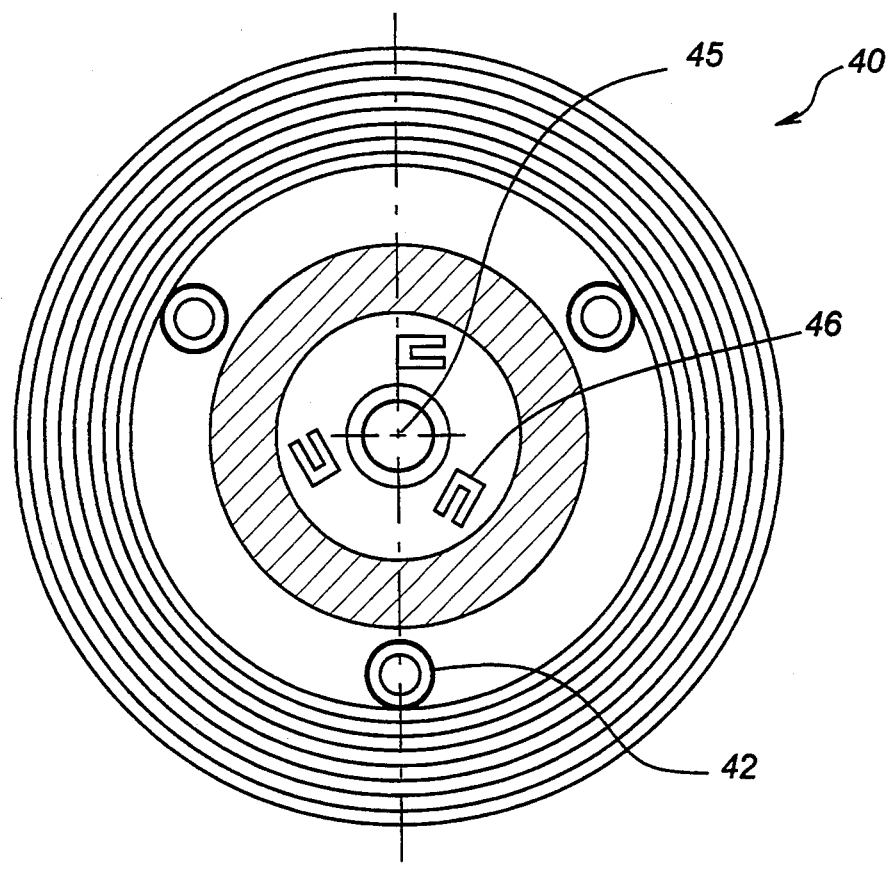
Figure 5C:
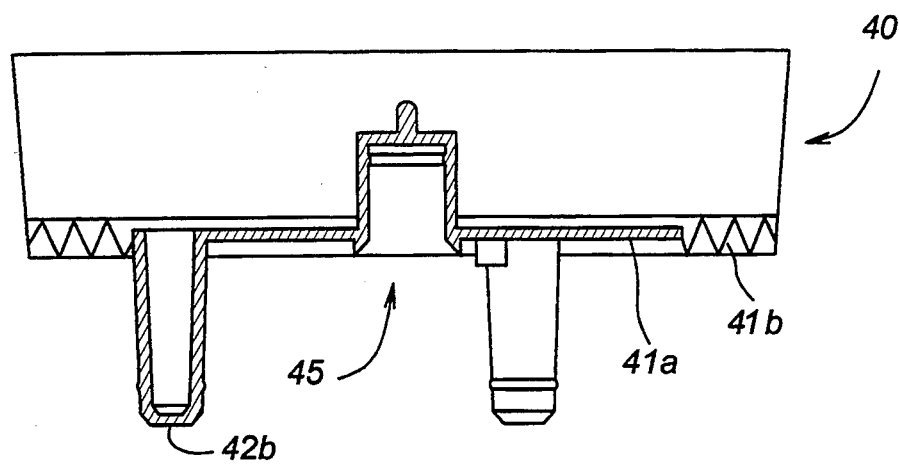
Figure 5D:
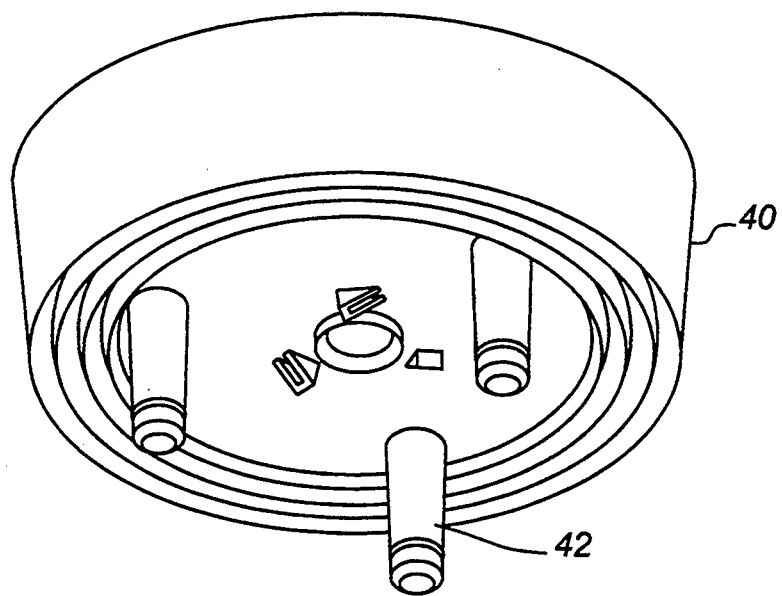

Referring to FIGS. 4a–4d, FIGS. 5a–5f and FIG. 15, a liquid specimen collection container indicated generally by reference numeral 30 comprises an upper sample chamber 29 having an upper access opening 31, a lower sample chamber 32 releasably engageable with the upper sample chamber 29, a flow passage 33 connecting upper chamber 29 and lower chamber 32 to conduct liquid from the upper sample chamber 29 to the lower sample chamber 32, and a container closure and seal generally indicated by reference number 34, engageable with the upper sample chamber 29 to close upper access opening 31 and seal upper sample chamber 29 and lower sample chamber 32 adjacent the flow passage 33. The container closure or top 34 comprises a lid 35, sealingly engageable with upper sample chamber 29, suitably as by exterior threads 36 on lid 35 and interior threads on chamber 29. Container closure 34 further comprises a vertical column 37 joined to lid 35 at a first end 37a of the column, an upper plug portion 38 of the column at a second end 37b of the column sealingly engageable with upper sample chamber 29 adjacent passage 33 in an upper portion 33a thereof, and a lower plug 39, releasably joined to the upper plug portion 38 to seal the lower sample chamber 32. Lower sample chamber 32 comprises a base 40, a variable volume bellows assembly 41 joined to base 40, at least one and as illustrated preferably a plurality of access apertures or nozzles 42 in a lower portion of bellows assembly 41, and a retaining element 43, suitably in the form of an annular keeper groove, to cooperatively engage a mating element 44, in the form of a projecting annular rim, on lower plug 39. A guide recess 45 is formed centrally in the underside of bellows assembly 41. The three nozzles 42 illustrated are spaced 120 degrees apart. The nozzles have a duct 42a opening into lower sample chamber 32 of container 30, and also have a closure 42b closing the duct remotely from the duct opening into the chamber 32. Closure 42b may be at the tip of the nozzle as shown in FIG. 5c, or may be positioned between the duct opening to chamber 32 and the nozzle tip. Nozzles 42 may additionally have flag structure 42c to indicate a primary and secondary nozzles. On the underside of bellows assembly 41 three ramp stops 46 are equally spaced between the nozzle ports. A plurality of upstanding vanes 47 radiate from the periphery of guide recess 45 to an upstanding annular tie 48 radially inward of a bellows portion 41b of bellows assembly 41. A floor plate portion 41a of the bellows assembly is radially inwardward from bellows portion 41b. A temperature crystal (not shown) may be glued to the interior of base 40 between the joinder of base 40 to bellows assembly 41 and the bottom rim of base 40. A tamper evident seal may be placed over lid 35 onto the outside of upper and lower sample chambers 29 and 32, and another seal may be placed across the mouth of base 40 over rim 40a. The portion of container 30 not including the container closure 34 is generally indicated by reference numeral 49 in FIG. 4b.

Liquid Specimen Container Rack

Figure 6A:
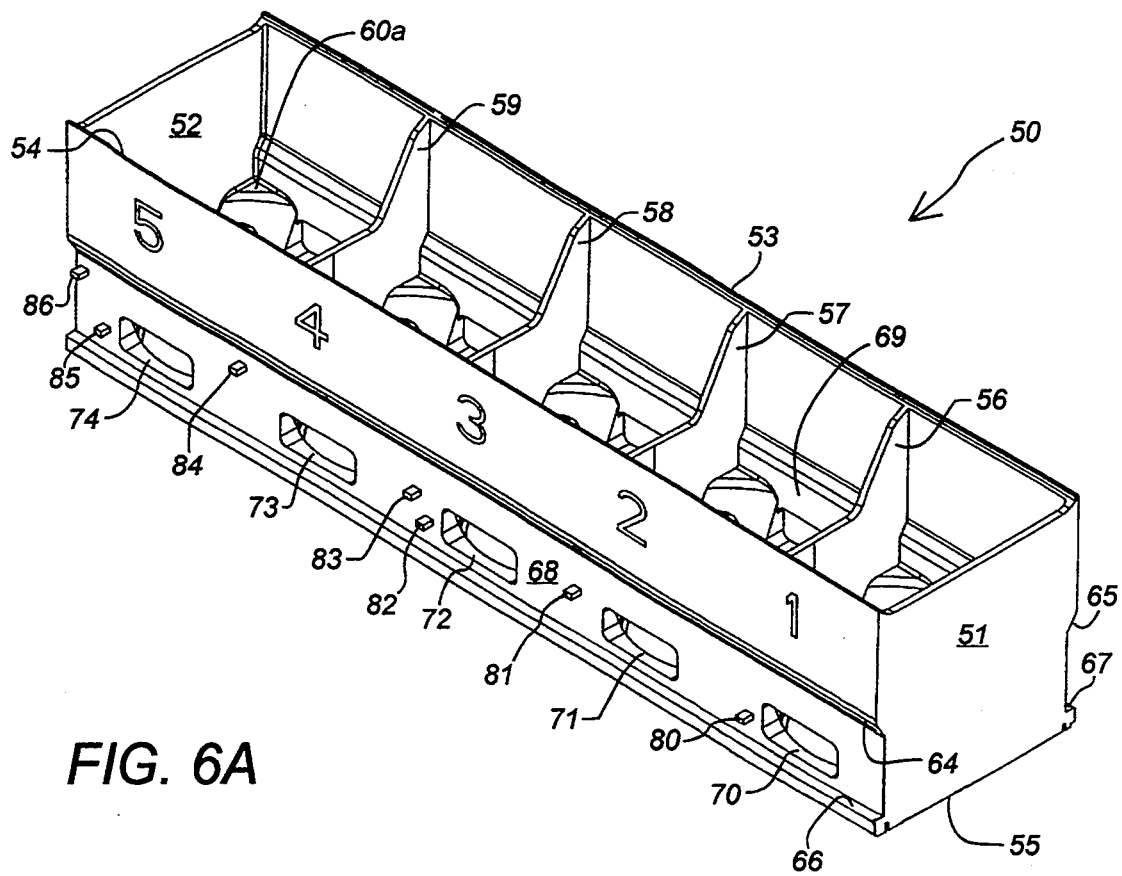
FIG. 6a and 6b is a rack device for containing a plurality of the specimen collection containers of FIGS. 4 and 5.
Figure 6B:
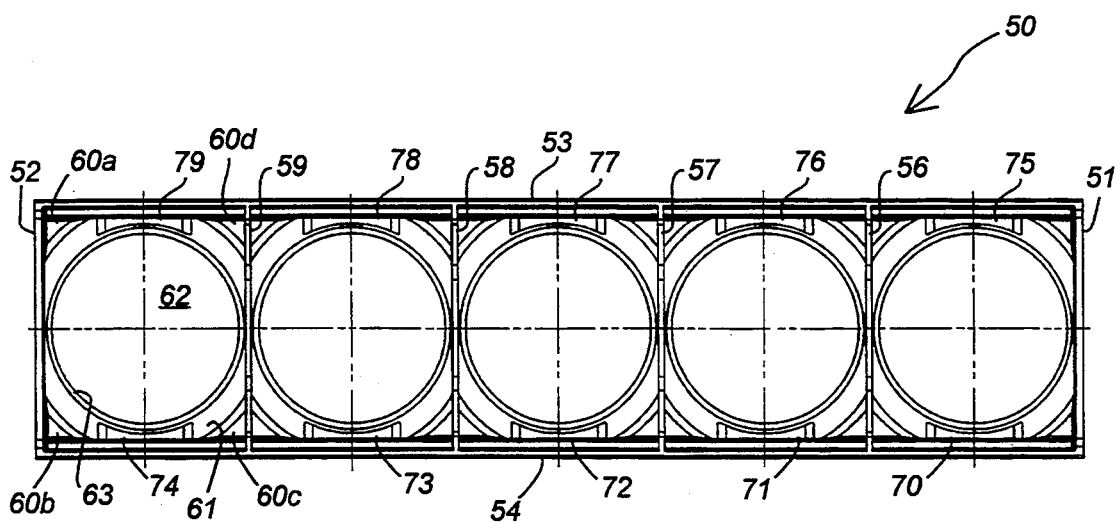
Figure 10:
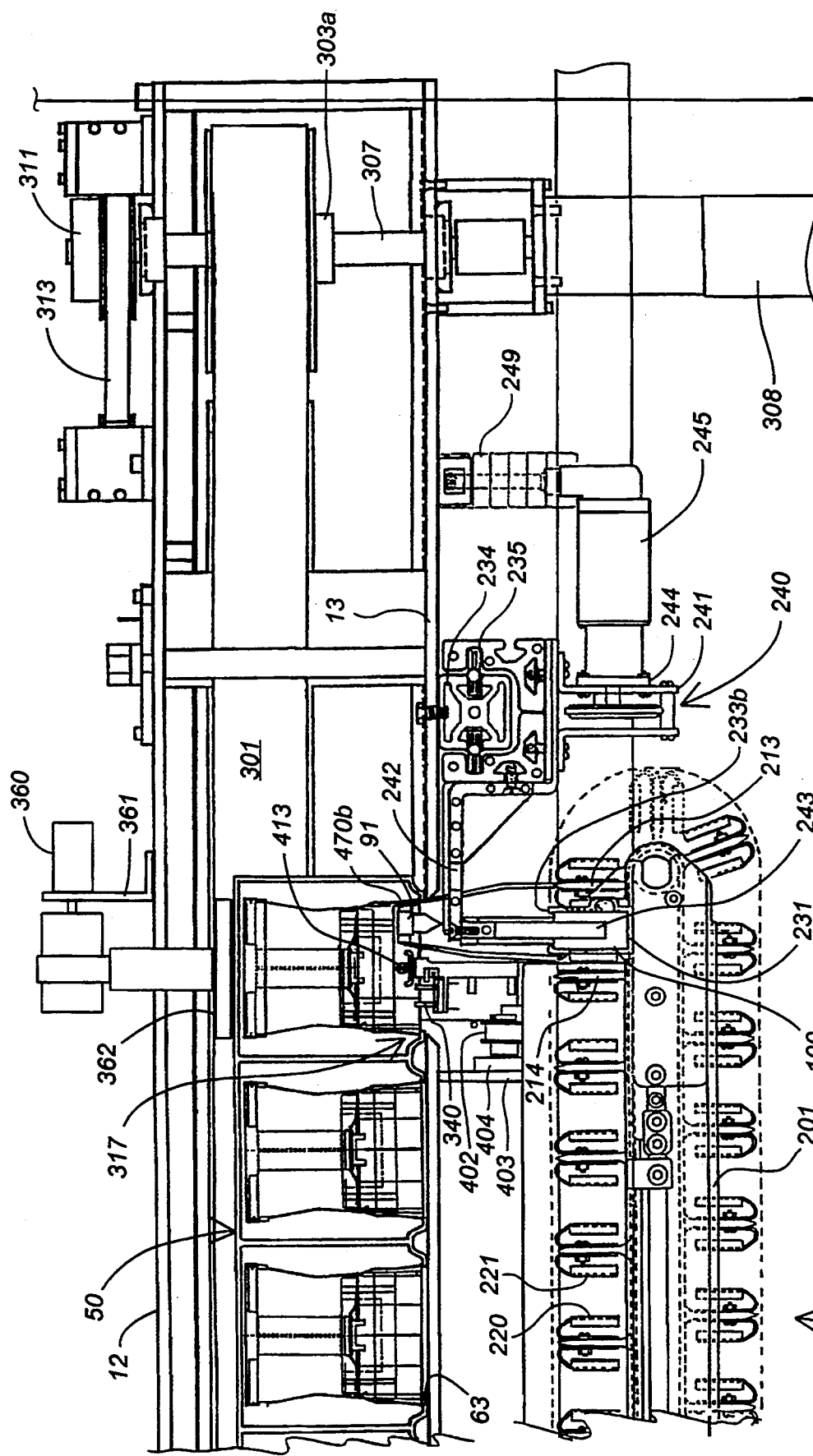
FIG. 10 is an enlarged view of a portion of the field in FIG. 8.

Referring to FIGS. 6a and 6b and also FIG. 10, a liquid specimen container rack is illustrated, indicated generally by reference numeral 50. Rack 50 includes front wall 51, rear wall 52, side walls 53 and 54 interconnecting front and rear walls 51 and 52, base 55 interconnecting walls 51, 52, 53 and 54, and partitions 56, 57, 58, and 59 interconnecting side walls 53 and 54 and providing five compartments in rack 50 identified as compartments "1" through "5" by legends embossed on the exterior of at least one sidewall, e.g. sidewall 53. Each of the front and rear walls 51 and 52 provide a location for placement of a bar code label identifying the rack. Base 55 comprises a plurality of corner horizontal braces 60a, 60b, 60c and 60d and a downwardly sloping annular portion 61 surrounding a circular base opening portion 62 in a floor 63. Compartments 1–5 each accommodate a liquid specimen container 30.

Sidewalls 53 and 54 of rack 50 are stepped in at a lower portion thereof at shoulders 64, 65 and stepped out at floor feet 66, 67 to form longitudinal recess portions 68, 69. A plurality of slot windows 70, 71, 72, 73 and 74 are formed in recess portion 68, and a plurality of slot windows 75, 76, 77, 78 and 79 are formed on the opposite sides of compartments 1, 2, 3, 4, and 5 in recess portion 69. The slot windows permit a bar code reader to read a bar code label placed on the exterior of base 40 of container 30, for identification of the container.

Three elevation of nibs project from each of sidewall recess portions 68, 69. Lower elevation nibs 80, 82 and 85 project from recess portion 68 longitudinally rearward of, respectively, slot windows 70, 72 and 74, intermediate elevation nibs 81 and 83 project from recess portion 68 longitudinally rearward of, respectively, slot windows 71 and 72, and upper elevation nibs 84 and 86 project from recess portion 68 longitudinally rearward of, respectively, slot windows 73 and 74. Intermediate elevation nibs 81 and 83 are longitudinally spaced from slot windows 71 and 72 more than lower elevation nibs 80 and 82 are. Upper elevation nibs 84 and 86 are longitudinally spaced from slot windows 73 and 74 more than intermediate elevation nibs 81 and 83 are longitudinally spaced from slot windows 71 and 72. The nibs provide an interruption of a light path for an optoelectrical sensor in apparatus 10. Placement of the nibs at three elevations permits a ternary coding system or $2^3$ signal combinations. The longitudinal spacing of the nibs is an accommodation for spaced optoelectrical sensors for the particular elevations of nibs. The arrangement of the nibs in FIG. 6a is merely one of any of the many arrangements possible with the ternary system. The ternary coding system identifies the particular compartment of rack 50 in which a particular liquid specimen container 30 is located. The nib identification of rack compartments permits rack 50 to be loaded into apparatus 10 without regard which end is the leading end and which is the trailing end.

Aliquot Receptacle and Aliquot Receptacle Holder

Figure 7A:
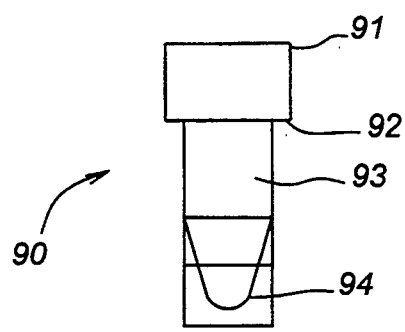
FIG. 7a illustrates an aliquot receptacle.
Figure 7B:
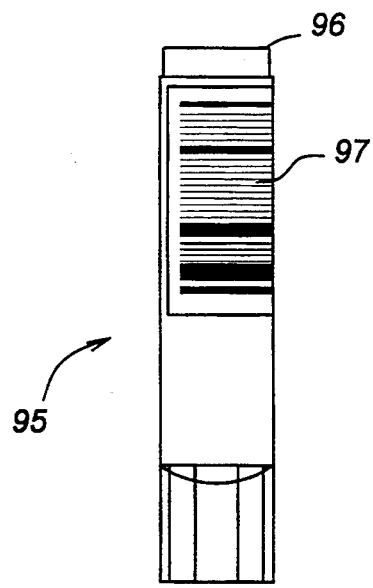
FIG. 7b illustrates a receiver tube into which the aliquot receptacle of FIG. 7a is insertable.
Figure 7C:
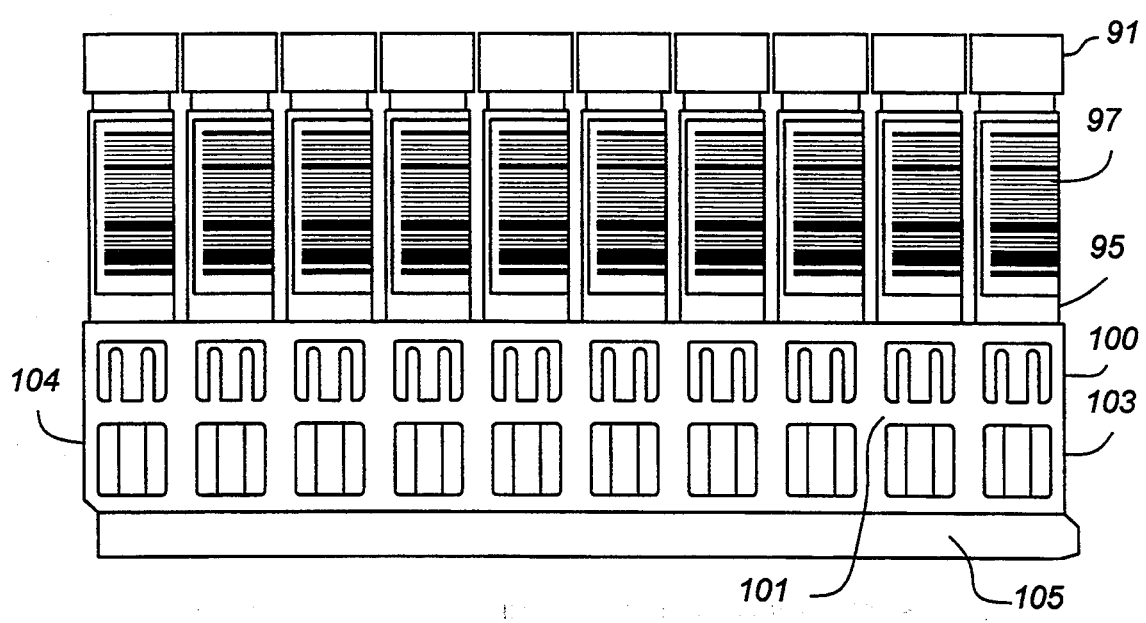
FIG. 7c shows an aliquot receptacle tube holder holding the aliquot receptacle and receiver tubes of FIGS. 7a and 7b.

Referring to FIGS. 7a–7c, FIG. 7a illustrates an aliquot receptacle or cup 90. Receptacle 90 has an upper flange portion 91 transitioning at shoulder 92 to a cylindrical intermediate barrel portion 93 that connects to a tapered lower portion 94. Receptacle 90 suitably has a volumetric capacity accommodating an aliquot of about 2 mL. FIG. 7b illustrates a receiver tube 95 into which the tapered and barrel portions 93 and 94 of aliquot receptacle 90 are insertable. The rim 96 of receiver tube 95 supports the shoulder 92 of flange portion 91 of aliquot receptacle 90, and suitably has a volumetric capacity accommodating an aliquot of about 7 mL. Bar code labels 96b are suitably applied to the upper portion of receiver tube 95.

FIG. 7c shows an aliquot receptacle tube holder 100 holding in a single column a plurality of bar code labeled receiver tubes 95 each supporting an aliquot receptacle 90. Aliquot receptacle tube holder 100 comprises a plurality of compartments formed over a base 105 by partitions between parallel sidewalls 101, 102 that unit front and rear ends 103 and 104. In the holder illustrated, nine partitions form ten compartments between front and rear ends 103 and 104.

Machine Systems

Apparatus 10 includes a number of cooperating systems: an aliquot receptacle holder input queue system 200, an aliquot receptacle holder track and mover system 225, a liquid specimen container rack track and mover system 300, a liquid specimen container and aliquot receptacle manipulation system 400, a liquid specimen container chamber opening and closing system 500, an aliquot receptacle holder output queue system 600, a machine off loader system 700, a controls and blinds system 800, and machine computer and control system 900.

Aliquot Receptacle Holder Input Queue System

Figure 8:
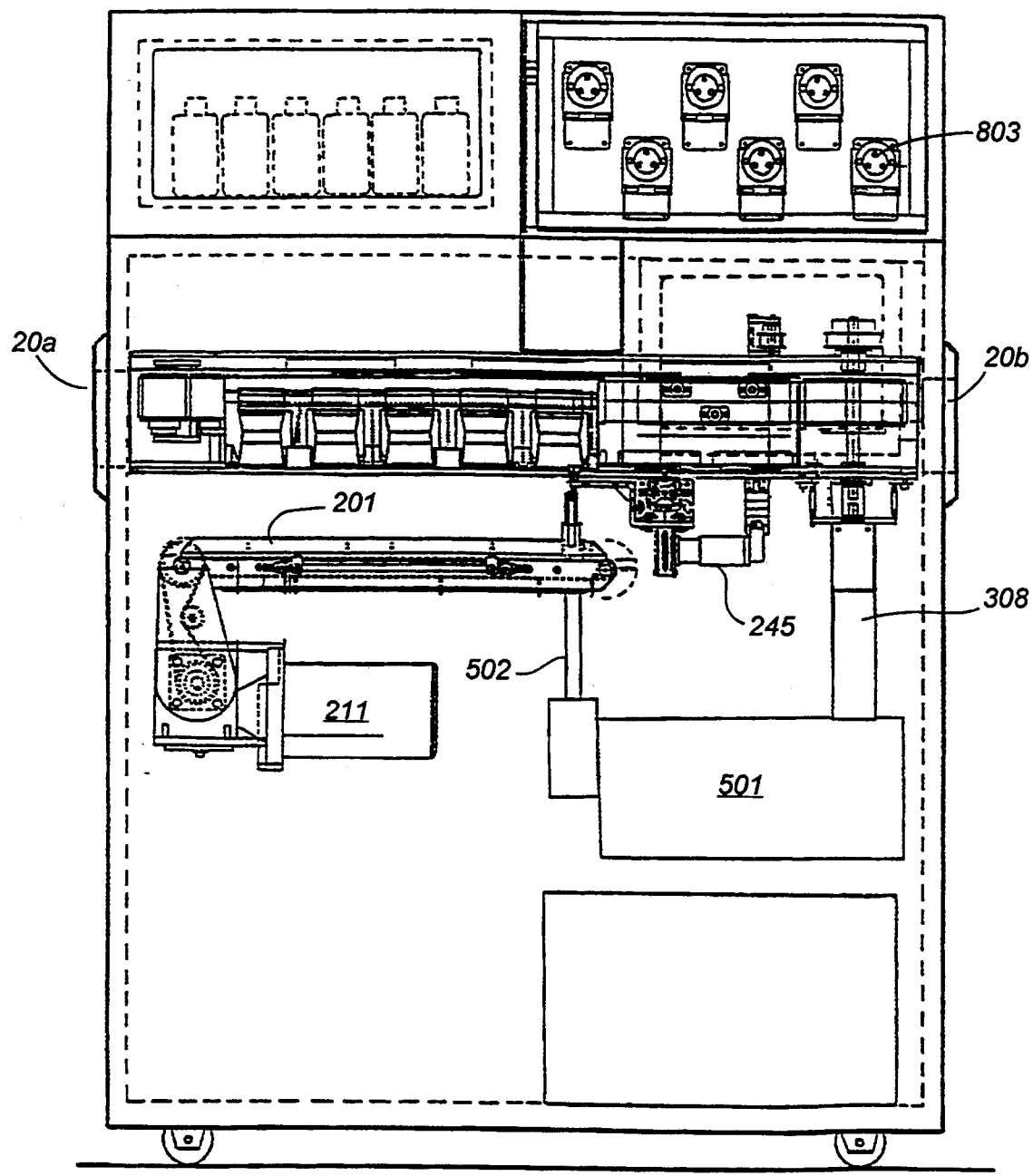
FIG. 8 is a partial sectional layout front view of the apparatus of FIGS. 1-3.
Figure 9:
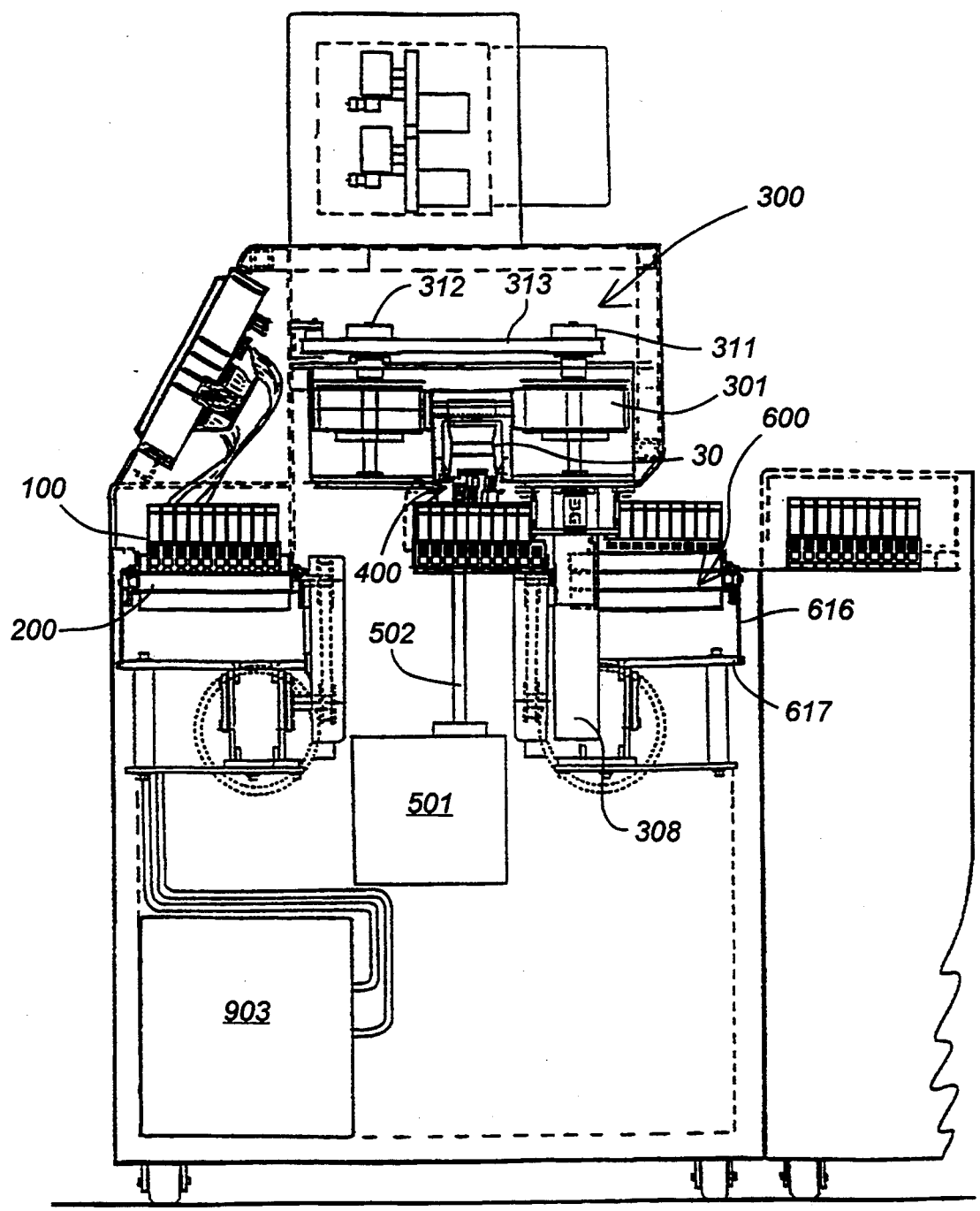
FIG. 9 is a partial layout right end view of the apparatus of FIGS. 1-3.

Referring first to FIGS. 9 and 13, an aliquot receptacle holder 100 is depicted in right end view at a front of queue position on an aliquot receptacle holder input queue system indicated generally by reference numeral 200. Referring to FIGS. 8 and 10 for a front view, aliquot receptacle holder input queue system 200 comprises an endless loop conveyor belt 201 carried on belt rollers 202, 203 supported by adjustable mounts 204, 205 connected to a frame member of framework 11. Belt roller 202 includes a pulley wheel 206 that is rotated by pulley belt 207 which at its other end is driven by driver pulley 208 rotating on drive shaft 209 of gear 210 connected to aliquot receptacle holder input queue drive motor 211. Belt cover 212 shields pulley belt 207. Aliquot receptacle holder input queue conveyor belt 201 includes stands 213, 214 etc. at regular aliquot rack intervals along the belt. The stands separate a plurality of aliquot racks in a queue on the belt and on rotation of the conveyor belt to the front of the queue, support and position each aliquot receptacle holder. Optionally, the stands may include spring tensioner spans 220, 221 on opposing stand faces to accommodate, support and center position a holder 100 between the stands. This allows some variation in aliquot receptacle holder dimensions. The outside edges of the conveyor belt have a hole centered between each pair of stands 213, 214 etc. Optoelectric emitter detector sensor pairs aligned to read light when a hole passes over the emitter of the pair are located above and below the conveyor belt.

Aliquot Receptacle Holder Track and Mover System

Referring to FIGS. 8, 10 and 13, an aliquot receptacle holder track and mover system 225 comprises an aliquot receptacle holder track 230, and an aliquot receptacle holder pusher carriage 240 and carriage rail 234 transverse to the direction of travel of aliquot receptacle holder input queue belt 201.

System 225 further comprises an aliquot receptacle holder pusher carriage drive d.c. closed loop servomotor 245 and power cable and support 249. As known in the art of drive motors, a servomotor includes an encoder (here suitably an optical wheel device) which provides an encoding signal for fractions of or whole revolutions of the drive shaft of the motor. In this invention, the machine computer system receives the signals and counts them. The count of signals is learned or set for a particular travel distance of a device driven by the motor. The machine computer system controls the revolutions of a drive servomotor for a predetermined count number to place the device driven by the servo motor at a particular position.

As best seen in FIGS. 10 (from the front), FIG. 3 (from the rear) and FIG. 13 (from the right side), aliquot receptacle holder track 230 is an channel connected to frame members of framework 11 and transversely spans the distance between an aliquot receptacle holder feed position on conveyor belt 201 at the front of aliquot receptacle holder input queue 200 and an aliquot receptacle holder receiver position on a conveyor belt 601 at the front of aliquot receptacle holder output queue 600. Channel 230 comprises both a smooth horizontal platform 231 of width to easily accommodate the width of an aliquot receptacle holder 100, and also upstanding sidewalls 232a, 232b which include infacing top flanges 233a, 233b to arc over the top of the sides of holders 100 as they travel channel 230 and retain holders 100 on the track when aliquot receptacles 90 are vertically lifted from the receiver tubes 95 in holder 100 as described below. Platform 231 is positioned at a height substantially the same as the elevation of aliquot receptacle holder input queue conveyor belt 201 and aliquot receptacle holder output queue conveyor belt 601, as indicated by the dashed line 231' in FIG. 11.

Figure 11:
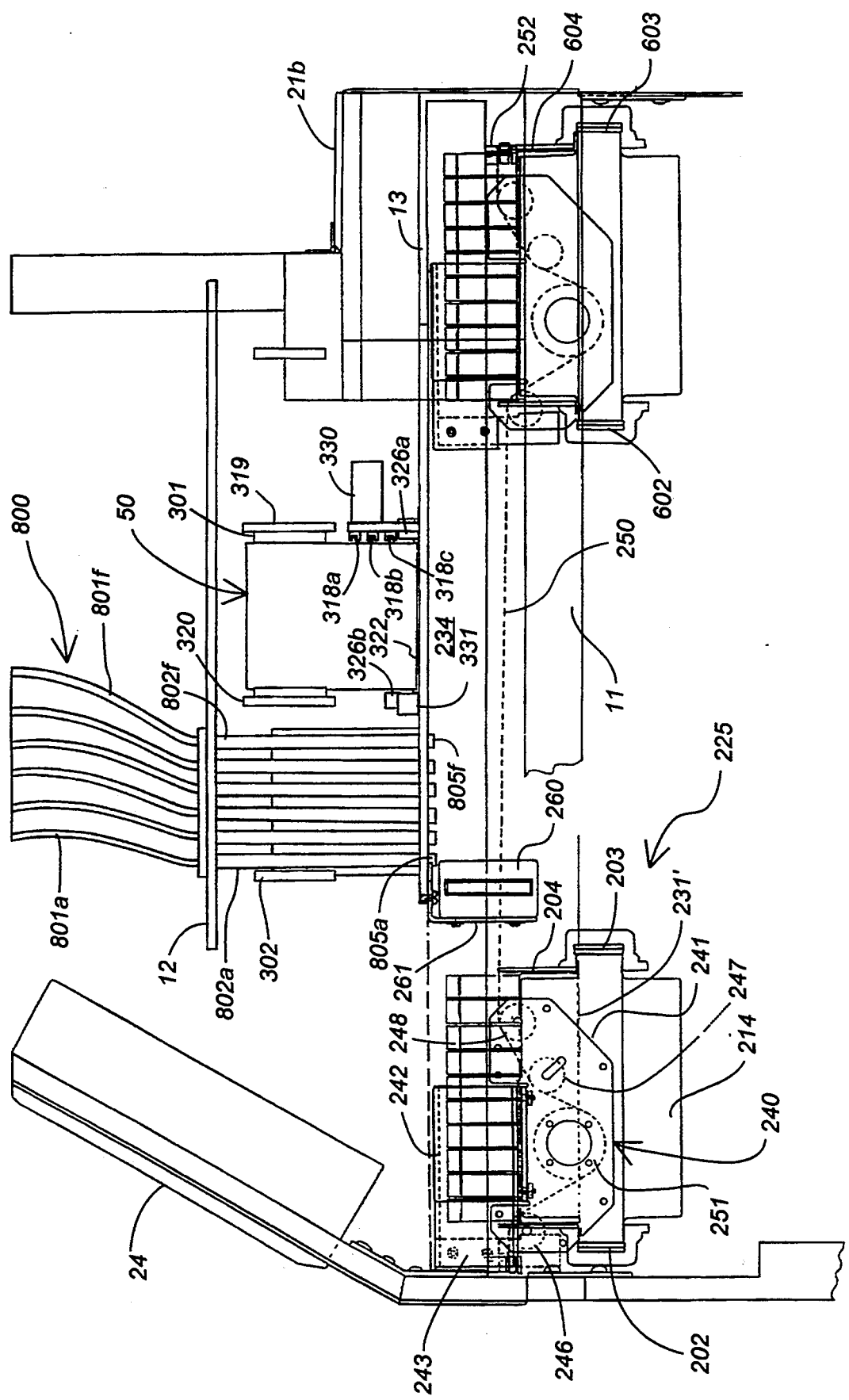
FIG. 11 is a partial sectional view taken along the line 11—11 in FIG. 8.

Referring to FIG. 11, an aliquot receptacle tube bar code reader 260 is connected by mount 261 to the front edge of bottom plate 13 and laterally adjacent the entrance of channel 230.

As best seen in FIGS. 10 and 11, an aliquot receptacle holder pusher carriage rail 234 parallel to aliquot receptacle holder track 230 is connected to the lower plate 13 of the apparatus 10 support structure. Mounted on roller bearings 235 to aliquot receptacle holder pusher carriage rail 234 is an aliquot receptacle holder pusher carriage indicated generally by reference numeral 240. The aliquot receptacle holder pusher carriage comprises a carriage 241, a pusher arm mount 242 connected to carriage 236, a pusher arm 243 connected to pusher arm mount 242, and an aliquot receptacle holder pusher carriage drive servomotor mount 244 connected to carriage 240. Carriage 240 and pusher arm 243 (in partial dashed outline) are seen in FIG. 11, which illustrates aliquot receptacle holder pusher carriage in both the fully retracted position (to the view's left) and in the fully extended position (to the viewer's right). In the fully retracted position, aliquot receptacle holder pusher carriage pusher arm 243 is located to the left of an aliquot receptacle holder at the aliquot receptacle holder feed position at the front of aliquot receptacle holder input queue conveyor belt 201. Aliquot receptacle holder pusher carriage drive servomotor mount 244 supports aliquot receptacle holder pusher carriage drive servomotor 245, chain spool wheel 246, tensioning wheel 247 and tracking wheel 248. Aliquot receptacle holder pusher carriage drive servomotor 245 receives power through a power cable carried in a flexible chain 249 anchored at a rear portion of the apparatus support base. A plastic drive chain 250 is attached at one end to spool wheel 246 and threaded around the bottom of a toothed wheel 251 carried on the drive shaft of drive servomotor 245, then over tensioning wheel 247 and tracking wheel 248 to an anchor at chain clamp 252. Actuation of servomotor 245 drives carriage 240 and pusher arm 243 along rail 234 from the fully retracted position toward the fully extended position, pushing an aliquot receptacle holder in front of the pusher arm from the aliquot receptacle holder input queue feed position to an aliquot receptacle holder filling position on aliquot receptacle holder track 230. The machine central processing unit is programmed to drive servomotor 245 for the appropriate distance to reach the aliquot receptacle filling station on aliquot receptacle holder track 230. Alternatively the aliquot receptacle filling station may be indicated by a sensor adjacent the track to sense the leading edge of the aliquot receptacle holder and signal drive servomotor 245 to stop, the sensor being located at a position calculated to place the first aliquot receptacle at the aliquot receptacle filling station. The aliquot receptacle filling station is at an elevation lower than a higher or upper position in the apparatus where the specimen container is placed for transfer of liquid to the receptacle at the aliquot receptacle filling station. This higher or upper position in the apparatus where the specimen container is placed for transfer of liquid to the receptacle at the aliquot receptacle filling station is called herein the "container dispense station."

Controls and Blinds System

Referring to FIG. 11, a controls and blinds system 800 comprises a plurality of dispense conduits 801a–801f connect to dispense tubes 802a–802f which are vertically mounted in a column parallel and aligned over aliquot receptacle holder track 230 at controls and blinds pumping stations 805a–805f. Pumping devices 803a–803f located in the upper right cabinet of the apparatus (FIG. 1) deliver controls through at last two of the tubes for at least high and low range calibration checks used by an analytical machine receiving the holders 100 with filled aliquot receptacles. Blinds are received through the other of the tubes. Pumping devices 803a–803f pump controls and blinds from bottles located in the upper left cabinet of the apparatus (FIG. 1). The machine computer system normally will receive instructions from a remote computer controlling when controls and blinds are to be dispensed into the aliquot receptacle tubes. For example, a control may be added every 10 aliquot receptacles. Addition of blinds is normally randomized.

Specimen Container Rack Track and Mover System

Referring to FIGS. 3, 8, 9, 10 and 11, a specimen container rack track and mover system 300 comprises a pair of container rack positioning toothed belts 301, 302 supported on toothed rollers, rollers 303a, 303b for belt 301 and rollers 304a, 304b for belt 302. Roller 303a is mounted on drive shaft 307 of container rack positioning belts drive servomotor 308. Rollers 303b, 304a and 304b are supported respectively on roller shafts 306, 309 and 310 carried in bearings connected to upper plate 12 and lower plate 13. An extension of shaft 307 above upper plate 12 mounts a toothed drive wheel 311. An extension of shaft 309 above upper plate 12 mounts a toothed slave wheel 312. A toothed belt 313 passing around wheels 311 and 312 drives roller 304a, which rotates belt 302 clockwise about idler roller 304b. Drive roller 303a rotates belt 301 counterclockwise about idler roller 303b. Thus linked, the return run of belts 301 and 302 advance to the right in machine 10, coursing from portal entrance 20a to portal exit 20b. Pressure plates 319, 320 applied to the inside of the belt loops at the return run aid in adjusting tension of container rack positioning belts 301, 302. A slideway 321 including a floor 322 and side rims 323a, 323b is affixed to the longitudinal portion of lower plate 12 between belts 301 and 302. At the container dispensing station, the slideway floor includes an opening 317 suitably having a radius equal to the radius of the container base 40. Slideway 321 defines a container rack track 315 extending from container rack track entrance portal 20a to container rack track exit portal 20b.

An optoelectrical emitter 325a on one side of slideway 321 and an optoelectrical detector 325b across the slideway provide means for sensing the leading edge of container rack 50 when it is inserted in portal 20a. Detector 325 is switched when light from emitter 325a is interrupted by the leading edge of rack 50, and signals the machine computer system. This initiates a program routine that controls the container rack positioning belts drive servomotor 308 to advance the container rack. A second pair of optoelectrical emitter/detectors 326a, 326b is positioned across slideway 321 between pair 325a, 325b and container dispensing station 317. Interruption of the light signal at pair 326a, 326b sends a signal to the machine computing system to control servomotor 308 to continue driving belts 301,302 only for the appropriate distance from pair 326a, 326b calculated to place the lead container 30 in container rack 50 at container dispense station 317 on slideway 321 of rack track 315. FIG. 10 depicts lead container 30 in rack 50 located at a container dispense station 317 on track 315. Station 317 on track 315 is at an elevation that is the level of slideway 321. Referring to FIG. 10, the relative positions of aliquot receptacle holder 100 and lead container 30 in container rack 50 are also illustrated. Lead container 30 and receptacle 90 in tube 95 for receipt of an aliquot of liquid specimen are placed relative to one another so that receptacle 90 and tube 95 are at a level below container 50.

Referring to FIG. 11, container bar code reader 330 is located adjacent container dispensing station 317 at a level to read bar code labels on the lower chamber portion 32 of container 30 visible in a slot window 75–79 of container 30. A photodetector 331 on the opposite side of slideway 321 detects light from bar code reader. Interruption of the bar code reader light signifies a container is present in container dispensing station 317. A plurality of optoelectrical sensors 318a, 318b, and 318c are provided in elevationally and longitudinally spaced positions adjacent container dispense station 317. Sensors 318a–c each are a slotted optical switch type sensor in the form of a U-shaped channel. One arm of the channel contains a light emitter and the other arm contains a photosensitive light detector. Passage of one of the nibs on rack 50 through the slot between the arms of the channel sensor interrupts the light from the emitter arm, and the detector is switched from one state to another, sending a signal to machine computer system.

Indicated by lines in FIG. 10, a container hold-down motor 360 is supported by mounts 361 connected to upper plate 12. Motor 360 moves a container rack hold-down piston plate 362 to a position only a slight tolerance gap, e.g. about 1/32 of an inch, above the top of lid 35 of container 30 in container rack 50.

Specimen Container and Aliquot Receptacle Manipulation System

Figure 12:
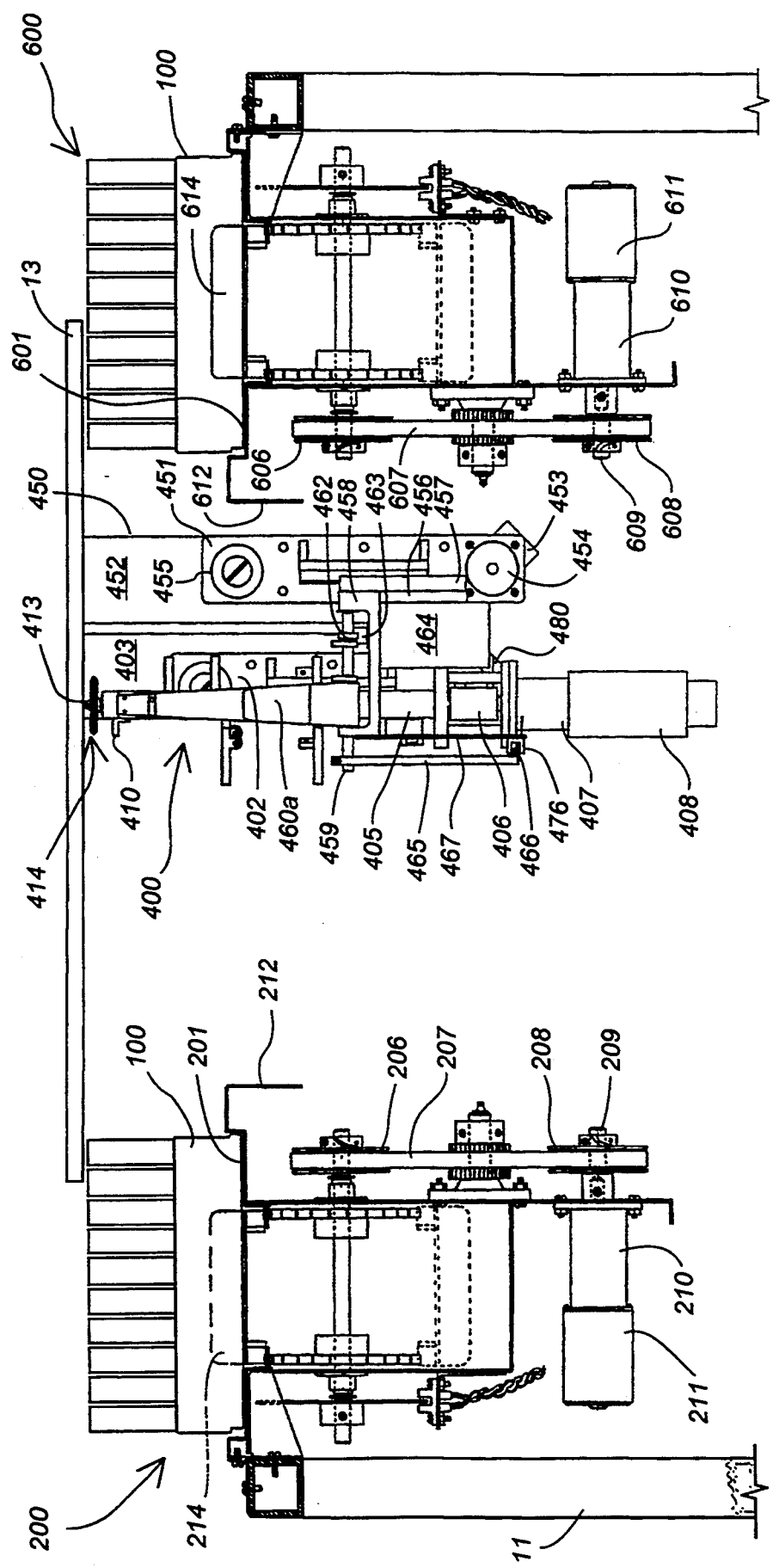
FIG. 12 is a partial sectional view taken along the line 12—12 in FIG. 8.

Referring to FIGS. 12, 13a–b, 14a–14c, and 17a–d, a liquid specimen container and aliquot receptacle manipulation system is indicated generally by reference numeral 400 and is located below the level of container rack 50 at the container dispense station 317 to the left of aliquot receptacle holder track 230. Referring to FIG. 12, liquid specimen container and aliquot receptacle manipulation system 400 comprises a container manipulation assembly indicated generally by reference numeral 401 and an aliquot receptacle manipulation assembly indicated generally by reference numeral 450.

Container manipulation assembly 401 comprises a linear bearing slide assembly 402 supported by mount 403 to framework 11 of apparatus 10. The movable belt clamp slide of linear bearing slide 402 is connected by fixture 404 to support sleeve 405. Actuation of vertical drive servomotor 480 for assembly 402 raises and lowers support sleeve 405. Support sleeve 405 is connected by coupling 406 to gearbox 407 of rotation drive servomotor 408. Actuation of rotation drive servomotor 408 rotates support sleeve 405. At the other end of support sleeve, a microswitch 410 is attached to the sleeve periphery. Microswitch 410 is radially spaced from the axis of support sleeve by a distance suitably equal to the radial distance from the axis of recess 45 of the container 30 to a point intermediate the distance between ramp ears 46 and a nozzle 42 of container 30. Closure of microswitch 410 occurs when support sleeve is being raised and microswitch 410 is pushed into an overhead object. Closure of microswitch 410 signals the machine computer system to stop the vertical drive servomotor for assembly 402, halting upward movement of support sleeve 405.

Figure 13B:
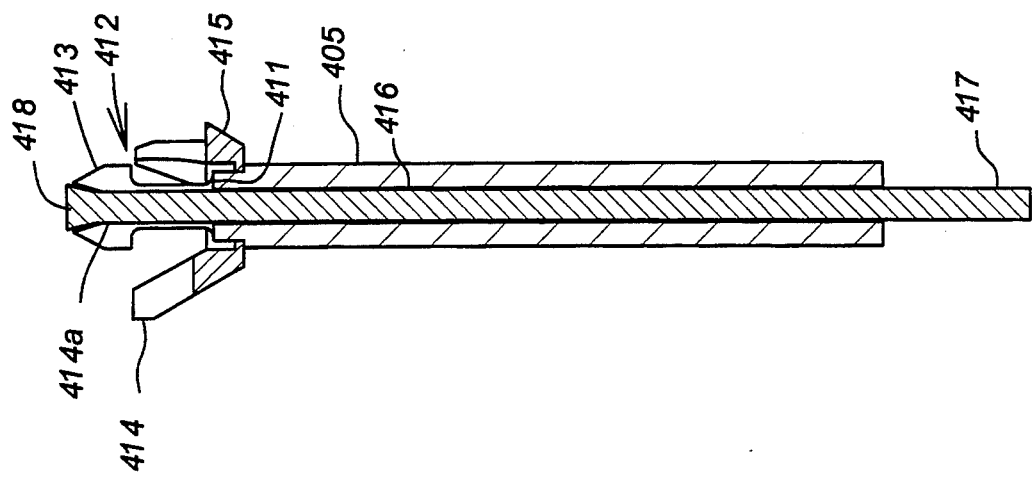
Figure 13A:
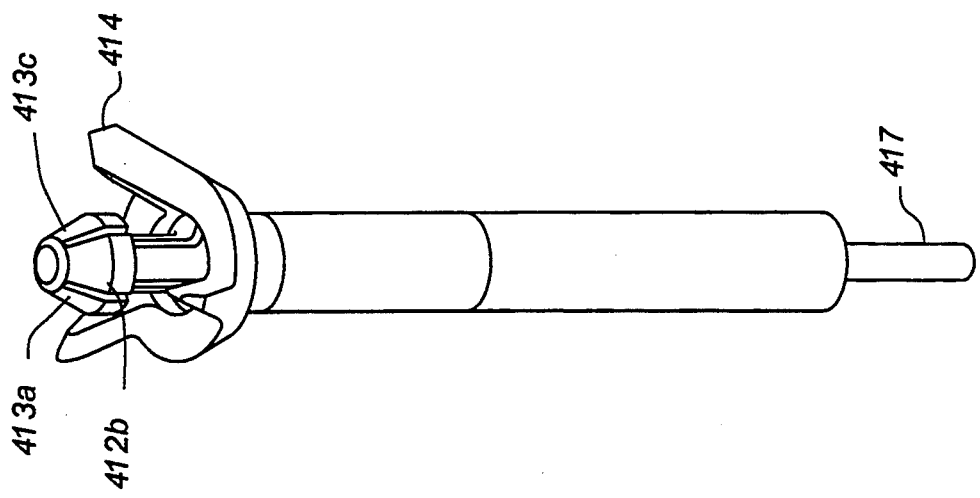
FIG. 13a is a perspective view of a container manipulation device in the apparatus of this invention.
Figure 14C:
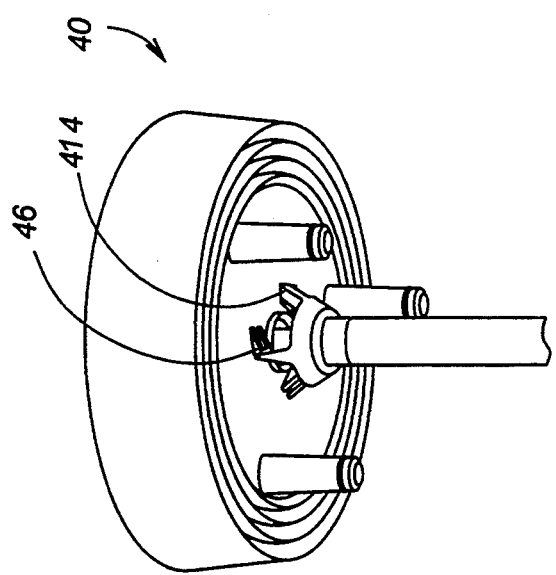
FIGS. 14a–14c are bottom perspective views illustrating the interaction of the container manipulation device of FIGS. 14a–14b and a container portion illustrated in FIGS. 5a–5d.
Figure 14B:
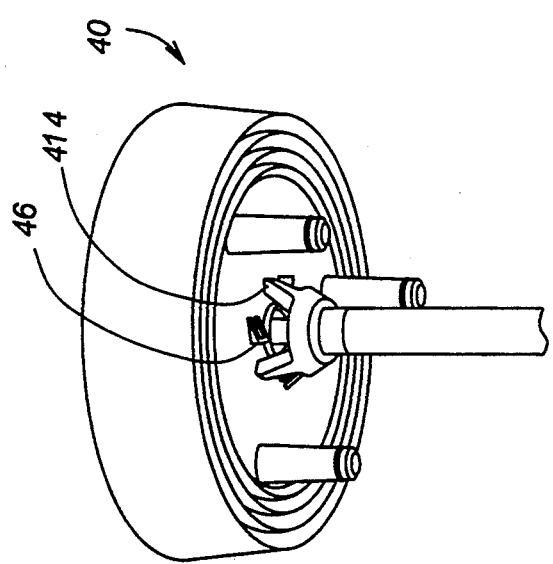
Figure 14A:
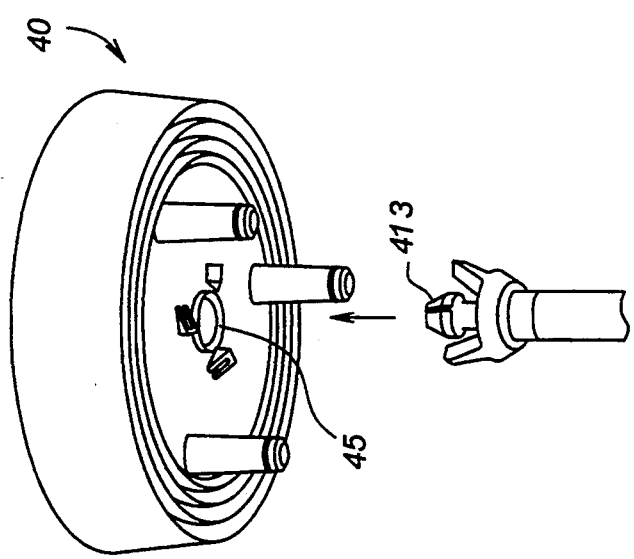

Referring now to FIG. 13a–b, support sleeve 405 terminates at a distal end which includes a peripheral shoulder 411. Surmounted and fixed on shoulder 411 is a driver/gripper piece 412 comprising a collet grip head 413 and a three pronged drive dog 414. Collet grip head 413 comprises four projections 413a, 4136b, 413c, 413d extending upwardly about a central bore 414a of an annular base portion 415 surmounted and fixed on shoulder 411. Central bore 414a is axially aligned with the axis of bore 416 of sleeve 405. Passing through central bore 414a of piece 412 and through bore 416 of sleeve 405 is a pull rod 417. The distal end of pull rod 417 has an enlarged radius portion 418. The most distal interior surfaces of collet gripper projections 413a, 4136b, 413c, 413d at the opening to central bore 414a are chamfered to permit pull rod enlargement 418 to be retracted into central bore 414a. Retraction of pull rod enlargement 410 spreads projections 413a, 4136b, 413c, 413d radially outward from central bore 414a.

Figure 16A:
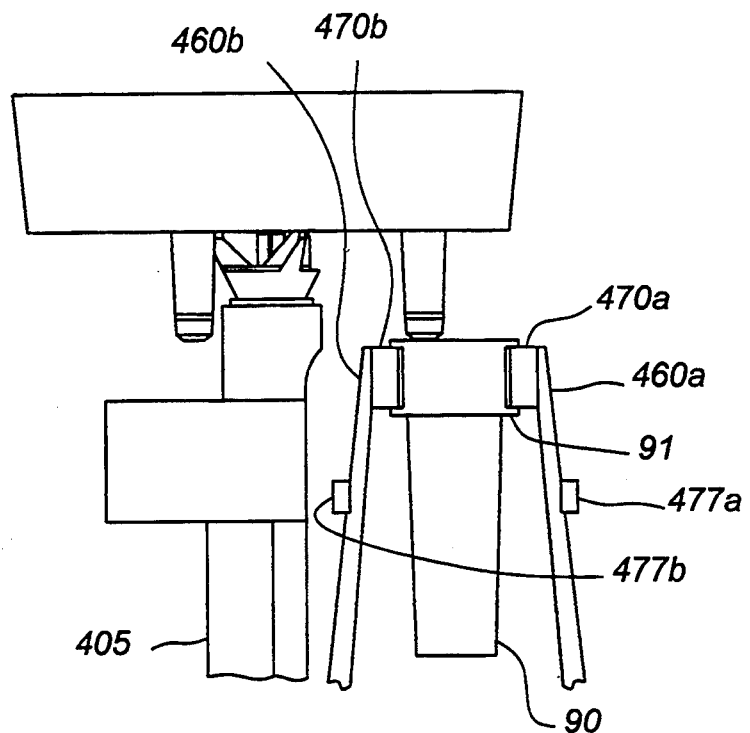
FIG. 16a is a side elevational view of an upper portion of the manipulation systems for a liquid specimen container and aliquot receptacle shown in FIGS. 12 and 13.
Figure 16B:
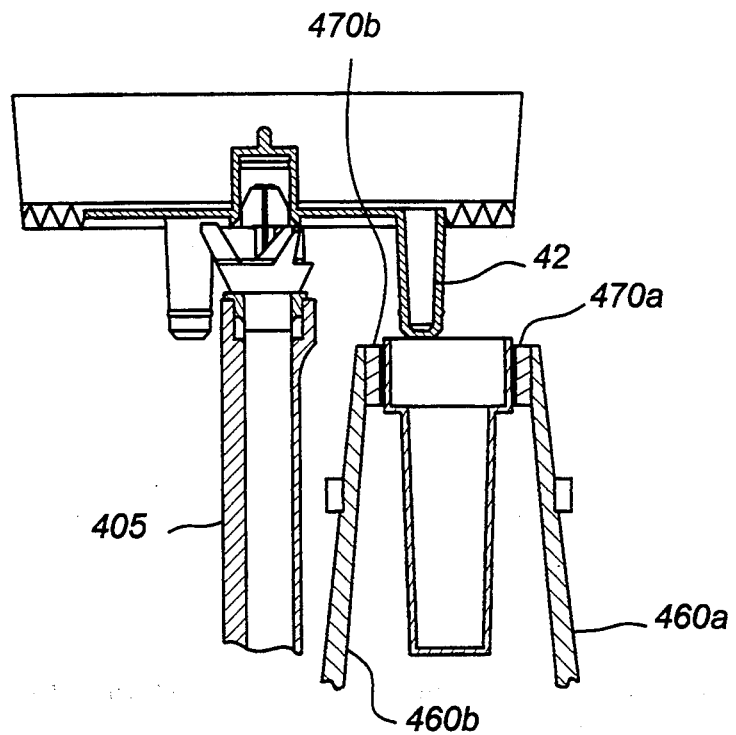
Figure 16C:
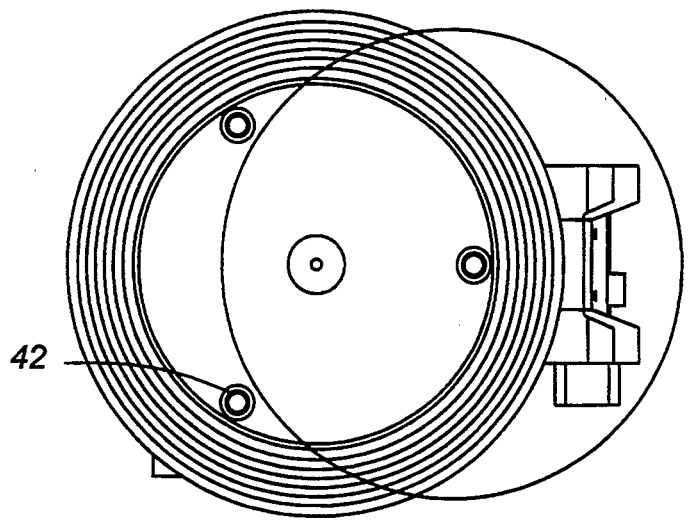
Figure 16D:
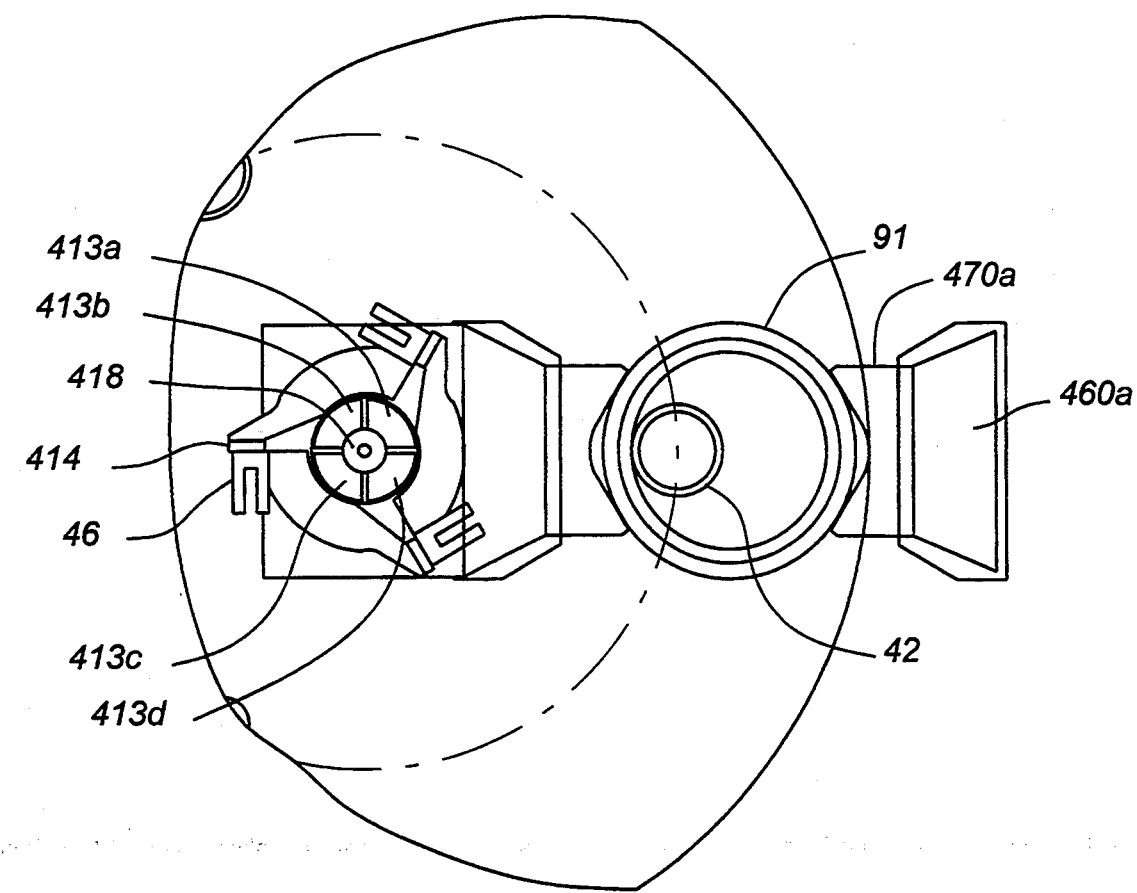
FIG. 16d is an enlargement of a portion of the field of FIG. 16c.

Referring back to FIG. 12, aliquot receptacle vertical drive assembly 450 comprises a linear bearing slide assembly 451 supported by mount 452 to framework 11 of apparatus 10. A linear bearing slide assembly vertical drive servomotor 453 drives pulley wheel 454. A pulley belt (not visible) running between drive pulley 454 and idler pullet 455 is clamped between plates 456 and 457. Plate 457 is fixed to yoke 458. Actuation of vertical drive servomotor 453 moves the pulley belt and clamp plates 456 and 457 and so also yoke 458 in the direction of pulley belt movement. This raises and lowers yoke 458. Yoke 458 supports dowel 459 in bearing mounts. Dowel 459 transversely passes through longitudinal slots in each of the members of a pair of parallel arms each mounted normal to pivot bases of tong pair members 460a and 460b. Vertical displacement of dowel 459 pivots tong members 460a and 460b on the member's pivot base. Dowel up movement spreads the tong members; dowel down movement closes the tong members. Referring to FIGS. 16a, 16b and 16d, the distal ends of tong members 460a and 460b include clamp members 470a and 470b. In their home position, tong members 460a and 460b are open and extend upwardly on either side of aliquot receptacle holder track 230 at dispense station 317 with the clamp members 470a and 470b at a level even with the upper flange portion 91 of aliquot receptacle 90. Raising and lowering yoke 458 raises and lowers tongs 460 vertically astride track 230. Link 462 connects dowel 459 to plunger 463 of solenoid 464 also mounted to yoke 458. Actuation of solenoid 464 drives link 462 and dowel 459 vertically upwardly, pivoting the distal ends of tong members 460a and 460b toward each other. This causes clamp members 470a and 470b to clamp the upper flange portion 91 of aliquot receptacle 90. Attached to the distal end of dowel 459 is wand 465. The dependent distal end of wand 465 carries a flag 466. Attached to the distal end of yoke 458 is a stalk 467. The distal end of stalk 467 carrys two optoelectric channel switches 475, 476 of the type described for switches 318. Displacement of dowel 459 moves wand 465 and flag 466. If clamp members 470a and 470b have grasped aliquot receptor 90, the closing movement is stopped by flange portion 91 of aliquot receptor 90. This limits movement of flag 466 to a location between the channel sensors of the first optoelectrical switch 475, activating it to signal that clamp members 470a and 470b have grasped aliquot receptor 90. If no aliquot receptacle is present for clamp members 470a and 470b to grasp, the closing movement is not stopped as soon and the tong members overswing to a limit position. This further movement puts flag 466 at a location between the channel sensors of the second optoelectrical switch 476, activating it to signal to the machine computer system that an aliquot receptor is not present below container dispense station 317.

Referring to FIG. 16a, a pair of optoelectric sensors 477a, 477b are mounted on tong members 460a, 460b at a level determined to be intermediate the flange portion 91 and the bottom of aliquot receptacle 90 when flange portion 91 of aliquot receptacle 90 is grasped by tong clamp members 470a, 470b.

Liquid Specimen Container Opening/Closing System

Referring to FIGS. 3 and 15a–c, reference numeral 500 indicates a laser piercing and sealing system for opening and closing the primary liquid chamber of liquid specimen container 30. A laser assembly housing 501 houses a laser 502, a solenoid actuated shutter 503 and an electromechanically actuated lens 504. A power supply and an electronic controller 505 powers laser 502 and electronically controls the power supply, solenoid actuated shutter 503 and electromechanically actuated lens 504. When powered, laser 502 emits a laser beam in a column centered along an axis. Housing 501 is placed in apparatus 10 to direct the laser beam to the left of aliquot receptacle track 230 to a position in the column of dispense station position 317 that is radially spaced from the axis of bore 416 of container manipulation system support sleeve 405. That radial spacing is a distance equal to the radial distance between the axis of container guide recess 45 and the axis of a nozzle 42 of container 30. The beam is thus coaxial with a nozzle 42 when container 30, in rack 50 in dispense station position 317, is rotated about sleeve bore axis 416 to align a nozzle 42 with the laser beam. Laser lens 504 is positioned at an elevation between the laser and a nozzle tip closure 42 such that the focal length of the lens coincides with the closure of nozzle tip 42.

Aliquot Receptacle Output Queue System

Referring to FIG. 3, aliquot receptacle holder input queue system is indicated generally by reference numeral 600. Referring also to FIGS. 11 and 12, for a left end view, aliquot receptacle holder input queue system 600 comprises an endless loop conveyor belt 601 carried on belt rollers 602, 603 supported by adjustable mounts 604, 605 connected to a frame member of framework 11. Belt roller 602 includes a pulley wheel 606 that is rotated by pulley belt 607 which at its other end is driven by driver pulley 608 rotating on drive shaft 609 of gear 610 connected to aliquot receptacle holder output queue drive motor 611. Belt cover 612 shields pulley belt 607. Aliquot receptacle holder input queue conveyor belt 601 includes stands 613, 614 etc. at regular aliquot rack intervals along the belt. The stands provide slots for aliquot receptacle holders 100, separate a plurality of aliquot receptacle holders in the slots in a queue on belt 601, and on rotation of the belt 601, support and position each aliquot receptacle holder 100. Optionally, the stands may include spring tensioner spans on opposing stand faces as illustrated for 220 and 221 in FIG. 10 for input queue 200. The outside edges of the conveyor belt have a hole centered between each pair of stands 213, 214 etc. Optoelectric emitter detector sensor pairs aligned to read light when a hole passes over the emitter of the pair are located above and below the conveyor belt.

The slot position in queue belt 601 which is in longitudinal alignment with aliquot receptacle holder track 230 is in a receiver slot location. Optoelectric sensor 615 is mounted at the end of a pivot arm 616 pivotally connected to a support 617 mounted to the framework 11. In a home position a spring 618 connected to support 617 and pivot arm 616 maintains arm 616 and optoelectric sensor 615 in line with track 230 and the receiver slot location for belt 601 adjacent and to the rear of the receiver slot location. A solenoid is connected to pivot arm 615 and when actuated, the solenoid plunger pivots arm 615 clear of alignment with the receiver slot position. Pivot arm spring 618 returns pivot arm 616 to home position when the solenoid reverses.

Optoelectric sensor 616 is located at the other end of belt 601 adjacent and to the rear of the slot location at the end of the upper run of conveyor belt 601. These sensors detect the presence of a holder 100 in the slot to which the are adjacent. Thus sensor 615 detects if a holder is in the receiver position in alignment with track 230, and sensor 616 detects whether a holder 100 is at the end position of the upright run of conveyor belt 601.

Aliquot Output Receptacle Holder Off-Machine Transfer System

Figure 17:
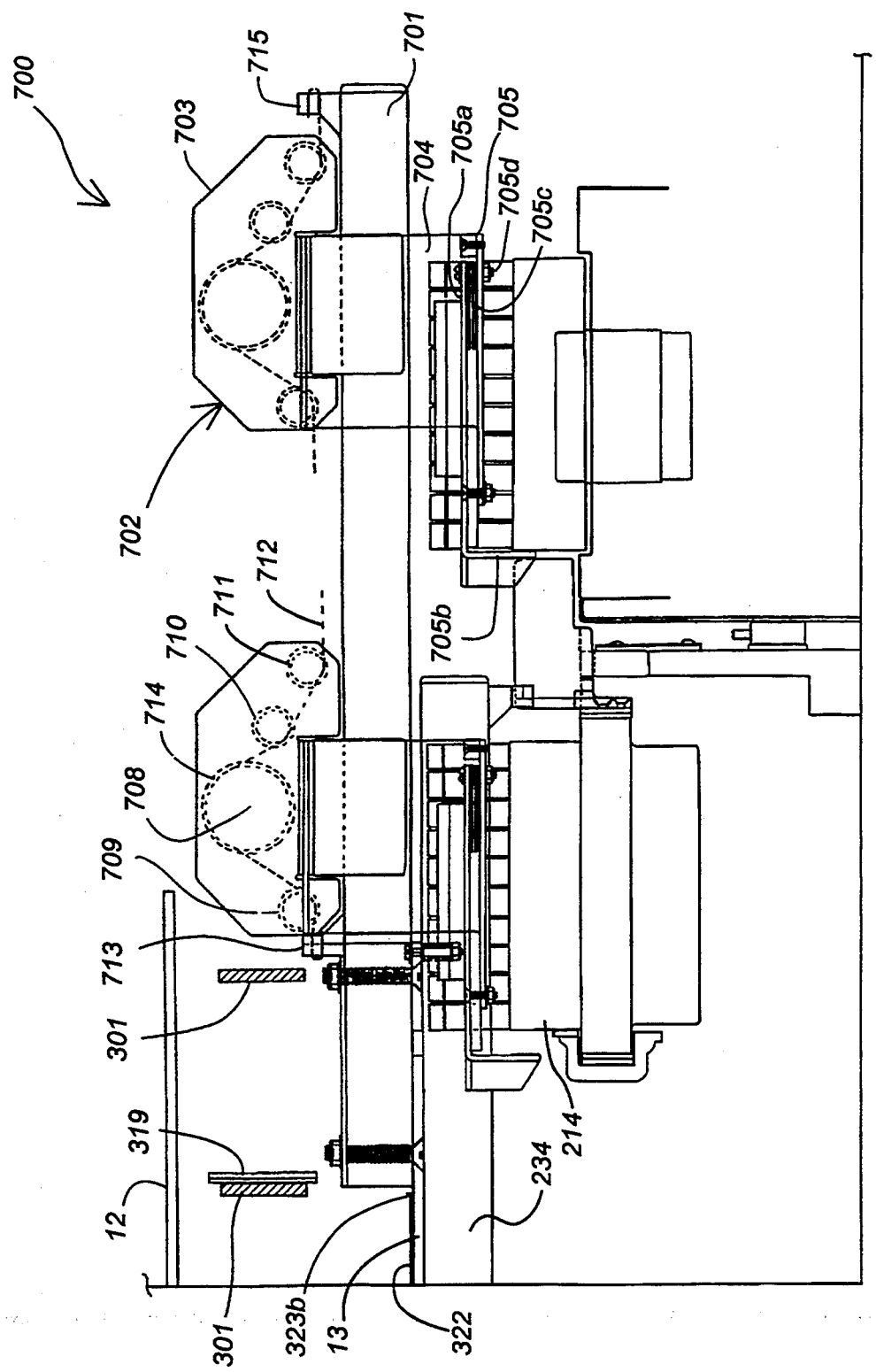
FIG. 17 is a partial sectional view taken along the line 18—18 in FIG. 8

Referring to FIGS. 2 and 17, reference numeral 700 generally indicates an aliquot output receptacle holder off-machine transfer system. Aliquot output receptacle holders on the aliquot output receptacle holder output queue belt are transferred off the machine by operation of this system. An aliquot output receptacle holder pusher carriage rail 701 parallel to and adjacent aliquot receptacle holder track 230 is connected to lower plate 13 above it. Rail 701 extends over aliquot receptor output queue. Mounted by roller bearings to rail 701 is an aliquot output receptacle holder pusher carriage indicated generally by reference numeral 702. Aliquot output receptacle holder pusher carriage 702 comprises a carriage 703, a pusher finger assembly mount 704 connected to carriage 703, a pusher finger assembly 705 connected to pusher finger assembly mount 704, and an aliquot output receptacle holder pusher carriage drive servomotor mount 705 connected to carriage 703. Pusher finger assembly 705 includes proximal horizontal member 705a, distal vertical member 705b, and spring 705c. Proximal horizontal member 705a is hinged about pivot 705d. Spring 705c urges proximal horizontal member 705a against mount 704. This places distal vertical member 705b in alignment with aliquot receptacle holder track 230. FIG. 18 illustrates carriage 703 and pusher finger assembly 705 in both the fully retracted position (to the viewer's left) and in the fully extended position (to the viewer's right). In the fully retracted position, also seen in FIG. 3, vertical pusher finger 705b of assembly 705 is located to the (viewer's) left of an aliquot output receptacle holder in the receiver slot position on conveyor belt 601. Aliquot output receptacle holder pusher carriage drive servomotor mount 706 supports aliquot output receptacle holder pusher carriage servo drive motor 708, idler wheel 709, tensioning wheel 710 and tracking wheel 711. A plastic drive chain 712 is attached at one end to anchor 713 and threads around idler wheel 709, the bottom of a sprocket wheel 714 carried on the drive shaft of servo drive motor 708, then over tensioning wheel 710 and tracking wheel 711 to an anchor at chain clamp 715. Actuation of servomotor 708 drives carriage 703 and pusher finger assembly 705 along rail 701 from the fully retracted position toward the fully extended position.

As best seen in FIG. 3, a guide plate 716 is mounted horizontally on lower plate 13 between aliquot receptacle output queue conveyor belt 610 and container dispense station 317. Guide plate 716 has a vertical slot 717 formed therein defining a slot run having an entrance portion and a slot terminal portion. The entrance portion of slot 717 preferably is essentially parallel to aliquot receptacle holder track 230 aligned over track 230. The terminal portion of slot 717 is arcuate. The arcuate portion of the slot curves toward the machine right end away from track 230. As carriage 703 and pusher finger assembly 705 moves to its fully retracted position, the pusher finger 705b on the hinged member slides into the slot and follows the curve described by the slot. This moves finger assembly 705 out of the line of travel of an aliquot receptacle holder pushed by pusher arm 243 along track 230.

Machine Computer and Control System

The operation of the machine systems described above is performed under control of a machine computer system 900 which receives inputs from a keyboard such as at 901 (FIG. 1), from a remote computer connecting to the onboard machine computer system through a suitable connector, from machine sensors and machine servomotor encoders described above. The machine computer system suitably includes a master computer and a plurality of slave computer systems indicated generally by reference numeral 902 in FIG. 1 which control the machine systems through dc controllers indicated by reference numeral 903 that in turn communicate with and drive servomotors, drive motors, solenoids, relays and other electropowered devices. A machine power source 904 transforms line ac. power to machine dc power used by the electrical components of the machine computer and control system and the electrical components in communication with it.

Operation

A testing laboratory operating the apparatus 10 receives liquid specimen containers 30 from a place of specimen collection. The testing laboratory is a keeper of a chain of custody begun at the place of specimen collection. The apparatus and method of liquid specimen transfer from specimen container to aliquot receptacle provided by the present invention are instrumental in maintaining a chain of custody with assurance of specimen identity preservation while automating large scale aliquoting of the liquid specimen without invasive sampling procedures that could adulterate and disqualify the liquid specimen sampled.

At the place of specimen collection, a container in the partially assembled state shown in FIG. 4b is removed from a sealed wrapper. In a typical chain of custody procedure, the donor, after completing a multicopy requisition, is given the container portion 49 of the assembly. The collector retains the container closure 34. The donor privately urinates into the container portion 49 through upper access opening 31. Urine flows from upper sample chamber 29 into lower sample chamber 32 through flow passage 33. Lower sample chamber 32 fills, then upper sample chamber 29. The shape of the roof of lower chamber 32 assures very little air is trapped in the lower chamber as urine fills it and rises through flow passage 33 to occupy upper chamber 29. The donor returns the container 49 to the collector, who closes the container using closure 34. Closure 34 seals lower chamber 32 from upper chamber 29. The intrachamber pressure is the same as the ambient pressure of the situs of collection. The collector reads temperature strip to verify that the specimen is at body temperature (an authentic undiluted specimen) and places a tamper evident tape across lid 35 and onto the sides of the container. The donor initials the tape. The taped container is placed in one compartment of a two compartment mailing pouch. The requisition is signed by the donor and collector, a copy of it is given to the donor and a file copy is retained by the collector. The remainder of the requisition is placed in the second compartment of the pouch. The pouch is then delivered to the operator of apparatus 10. The bellows assembly 41 of container 30 permits lower chamber 32 to expand upon exposure of the container to any materially lower ambient pressure either during transit or at the destination site. Conversely, the bellows assembly 41 of container 30 and the small amount of air permitted captured by the roof of lower chamber 32 during chamber filling permit lower chamber 32 to contract upon exposure of the container to any materially higher ambient pressure either during transit or at the destination site. Bellows assembly 41 therefore assures that the ambient pressure changes to which the container is exposed do not cause the container to leak.

At the destination, the testing laboratory continues assurance of chain of custody of the container. A technician removes the container and the requisition from the pouch and attaches identical bar code labels from a set, one to the requisition, one to the upper half of the container and another to the lower half of the container. The label on the upper half assures that identification of the specimen in the upper half is the same as in the lower half. A batch of containers similarly handled and labeled is gathered for processing in a batch operation, typically abatch of 40 containers. A liquid specimen container rack 50 with a permanent bar code label is obtained, and five labeled containers 30 are placed in the rack. The technician reads the rack label with a bar code reader. Eight racks are processed in the same way to assemble the batch of 40 containers.

A machine operator gathers aliquot receptacle holders 100. As illustrated in FIG. 7c, these each hold ten aliquot receiver tubes 95 supporting aliquot receptacles 90. Bar code labels are on each receiver tube. The operator orients the tubes and labels in holder 100 so that when placed on aliquot receptacle holder input queue 200, the bar codes will face machine bar code reader 260. The operator then places each holder 100 onto aliquot receptacle holder input queue belt 201 between belt stands 213, 214 etc.

Normally the machine 10 will transfer aliquot receptacles filled by the machine directly through a receiver slot in the aliquot receptacle output queue conveyer (to be later described) and across a transfer bridge to the input feed chute of a specimen analyzing machine. Accordingly, the operator will verify that the output queue is clear. On occasion the analyzer will not be ready to receive specimen aliquots for testing, and in that instance, a startup routine for clearing the receiver slot of the aliquot receptacle output queue conveyer may be employed. A suitable routine may be as follows. The operator then powers up machine 10. At startup of the machine, optoelectrical sensor 615 detects any presence of an aliquot receptacle holder in the aliquot receptacle output queue belt at the aliquot receptacle holder receiver location holder 100 feed from aliquot receptacle track 230, and optoelectrical sensor 616 detects the presence of an aliquot receptacle holder in the aliquot receptacle output queue belt at the terminal upright position of the aliquot receptacle output queue belt run. If both optoelectrical 615 and 616 detect presence of an aliquot receptacle holder, the queue is assumed full, and the machine shuts down. If at startup only optoelectrical 615 detects an aliquot receptacle holder, it sends a signal to the machine computer system that causes it to activate appropriate controllers to energize aliquot receptacle output queue drive motor and index the belt in the direction away from the fill track until optoelectrical sensor 616 detects an aliquot receptacle holder. If at startup only optoelectrical sensor 616 detects the presence of an aliquot receptacle holder at the terminal belt run position, a signal is delivered to the machine computer system that causes it by the appropriate controllers to reverse aliquot receptacle output queue drive motor and drive the aliquot receptacle output queue belt in the direction toward the fill track until optoelectrical sensor 615 detects an aliquot receptacle holder. In either of the latter two instances, upon detection of an aliquot receptacle holder by optoelectrical 616, aliquot receptacle output queue belt is caused to move in the direction of the fill track. Then when optoelectrical 615 senses an aliquot receptacle holder it sends a signal to the machine computer system, and the machine computer system reverses aliquot receptacle output queue drive motor, indexing the belt in the forward direction one belt slot. Thus if any aliquot receptacle holders are on the aliquot receptacle output queue belt at startup and not in both the fill track receiver slot and the terminal belt run slot, this startup routine assures they are moved out of the fill track receiver slot position, and the belt is ready to receive at least one aliquot receptacle holder.

Upon startup, the machine computer system steps aliquot receptacle holder pusher carriage servomotor 245 through a predetermined number of revolutions, driving aliquot receptacle holder pusher carriage a known distance on rail 234, causing pusher arm 243 to advance holder 100 onto aliquot receptacle holder track 230 until lead tube 95 in holder 100 is at a label reading position in front of bar code reader 260. Reader 260 reads the label on the lead tube. Then, on signal from the machine computer system, drive servomotor 245 rotates sufficiently to advance the next trailing tube 95 to the label reading position in front of bar code reader 260. This step advance of holder 100 continues for every tube position in holder 100. If a label is mispositioned for reading or is absent, the reader sends an error signal to the machine computer according to the position in the holder 100.

The on-board computer of the machine receives input from a remote laboratory computer, connected by computer interface with the on-board computer, to place a control or blind in some aliquot receptacles traversing aliquot receptacle holder track 230. (Good laboratory practices may place a control liquid in every ten or so receptacles. A control is a liquid containing a specified amount of an analyte known to the operator of the analyzing machine which receives filled aliquot receptacles from machine 10. Controls are used to check calibration of the analyzing machine. A blind is a liquid containing an analyzed amount of an analyte not known to the operator of the analyzing machine. Blinds alter the otherwise predicatable order of filling aliquot receptacles with specimens, and are used to prevent dishonest operators from intervening and substituting fluids to falsify test results.) The on-board computer drives pusher carriage servomotor 245 and pusher arm 243 advances holder 100 to control and blind pumping stations 805a -805f. Under instruction from the remote computer, the on-board computer signals appropriate control and/or blind dispense pumps to dispense any programmed control liquids and any programmed blind liquids into the predetermined aliquot receptacles. After any dispense at control and blind dispensing station, carriage servomotor 245 and pusher arm 243 advances holder 100 on aliquot receptacle holder track 230 to specimen dispense station 317.

Independently of the foregoing movement of holder 100, the operator inserts a liquid specimen container rack 50 into machine entrance portal 20a. The bar code of rack 50 may be read by a bar code reader adjacent rack track 315 or by an off-machine remote reader. When rack 50 is inserted far enough, the leading edge of rack 50 interrupts light to photodetector 325b from photoemitter 325a, signaling the machine computer system, which activates rack belt servomotor 308. Motor 308 drives belts 301,302, which grip the sides of rack 50 and advance it along slideway 321. The leading edge of rack 50 then interrupts light to photodetector 326b from photoemitter 326a, signaling the machine computer system to commence a count of revolutions sensed from servomotor 308. When a predetermined number of counts have accumulated, the computer stops rack belt servomotor 308. The counts are those predetermined to place the lead container in specimen dispense station 317.

At specimen dispense station 317, photodetector 331 detects whether lead container position is empty. It is empty if light emitted from bar code reader 330 is received by photodetector 331. If detector 331 remains unswitched and the count to station 317 was accumulated, rack belt servomotor 308 is driven for a predetermined number of shaft revolutions calculated to advance rack 50 so that rack position "2" is situated over dispense station 317. If detector 331 is switched, rack position "1" is occupied by a container.

Figure 15C:
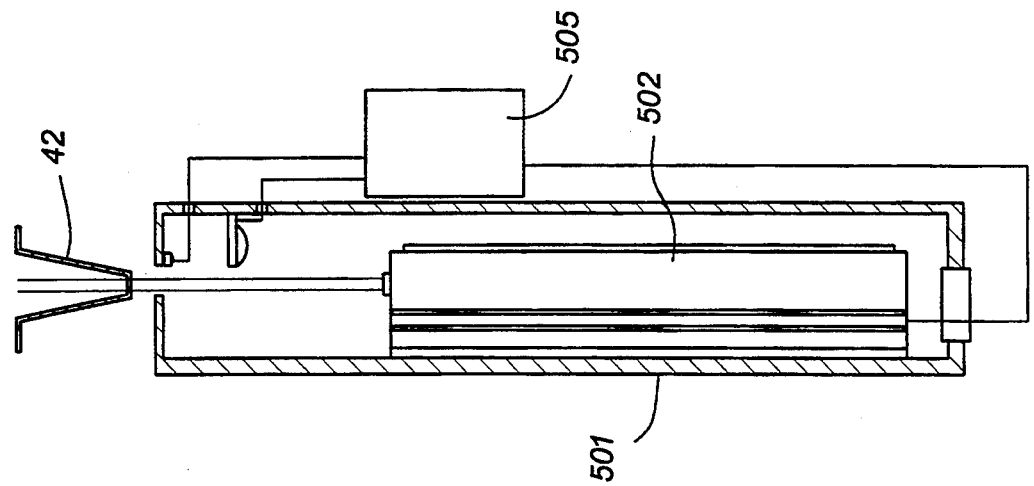
FIGS. 15a–15c are schematic views of a laser piercing and sealing system in an apparatus of this invention.
Figure 15B:
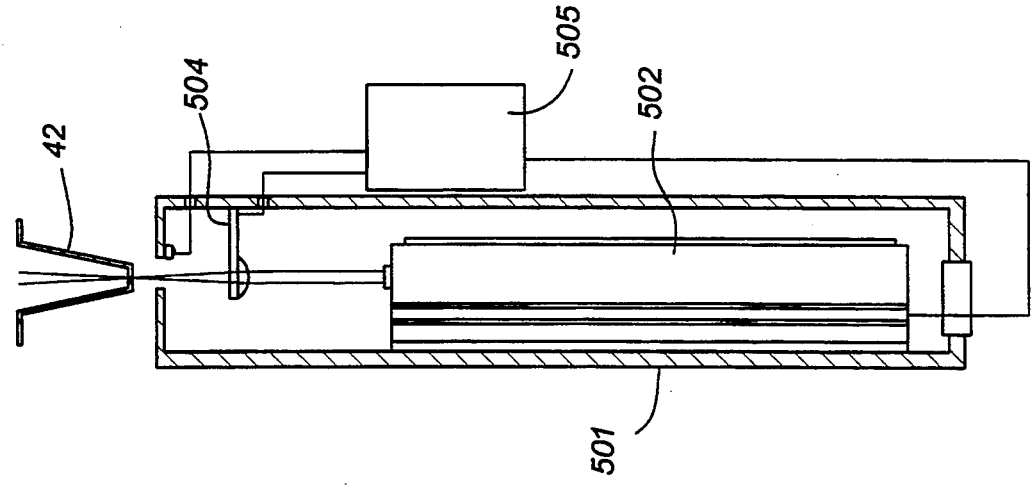
Figure 15A:
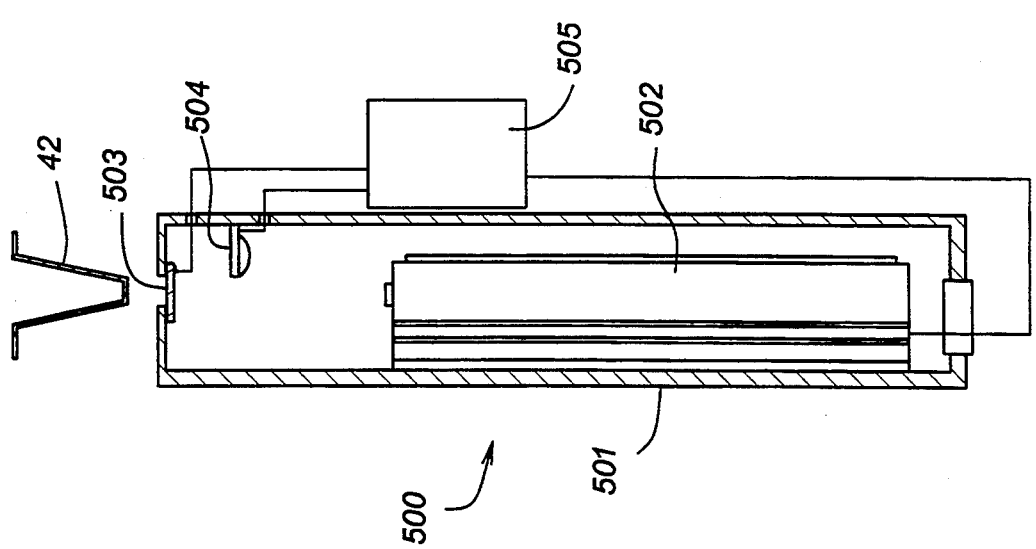

Switching by detector 331 initiates a pumping routine conducted by the machine computer. Support sleeve vertical drive servomotor 480 and support sleeve rotation drive servomotor 408 are actuated and rotatingly axially raise support sleeve 405. Referring to FIGS. 15a-c, collet grip head 413 and three prong drive dog 414 on sleeve 405 rotatingly axially spiral up and collet grip head coaxially enters guide recess 45. The correspondingly moving prongs of drive dog 414 spiral upwardly at a horizontal vector less acute than the ramp incline of ears 46 until microswitch 410 contacts the underside of bellows assembly 41. Upon contact with the underside of bellows assembly 41, support sleeve vertical drive servomotor 480 and support sleeve rotation drive servomotor 408 are switched off. Then sleeve rotation drive servomotor 408 is rotated a predetermined extent, more than 90 degrees and less than 180 degrees of rotation, suitably 140 degrees, to assure drive prongs 414a, 414b and 414c are firmly engaged with the vertical side of ramp ears 46 on the underside of bellows assembly 41. Then a solenoid coupled to pull rod 417 is activated by the machine computer system and pull rod enlargement 418 is retracted, radially spreading collet head 413 in guide recess 45, thereby gripping container 30. Support sleeve vertical drive servomotor 480 is then driven to elevate the container slightly off its seat in rack 50, suitably about 1/32 of an inch, to eliminate contact frictional resistance to rotation of container 30 in rack 50. Rotation drive servomotor 408 is then driven to spin container 30 two full turns. As container 30 spins, container bar code reader 330 reads the bar code label on the lower sample chamber through window 70 (assuming a container in position "1") in rack 50. Because the first part of the bar code could be already past window 70 when container 30 commences rotation and reader 330 commences reading, container 30 is spun twice to give at least one full bar code label passage across container bar code reader 330 to assure the reader begins a read at the start of the bar code label.

As container 30 is spun, staggered level optoelectric sensors 340 and 341 detect the presence of nozzles 42 relative to the machine computer system's encoding which is driving rotation servomotor 408. The two detectors also detect whether any of the nozzles 42 sweeping by them do not have the length required to interrupt the lower of the two sensors, sensor 341. This checks whether any nozzle has a tip that will not be at an elevation expected by the machine. For example, a differential in length may occur where the container previously has been accessed through a nozzle by truncating a nozzle tip to take a sample of the specimen. Alternatively, if a nozzle has collateral structure to identify it as a primary nozzle, as illustrated for example in FIG. 5f, the optoelectric sensors 340, 341 may be situated to read the passing nozzles for the presence or absence of the distinguishing structure. One revolution plus a few degrees is all that is required to read the nozzles, and the requirement is more than satisfied by the two revolution spin for the bar code label read. Passing the nozzles by sensors 340, 341 therefore locates the nozzles and optionally can discriminate among the nozzles to deselect a nozzle or select a nozzle.

Figure 5E:
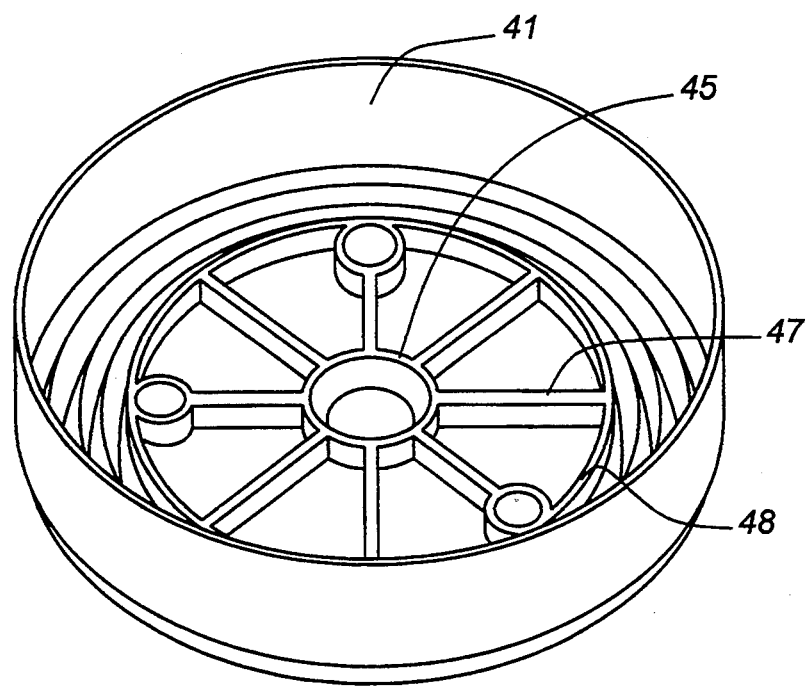

The spin of container 30 also serves to agitate the specimen in chamber 32 of container 30. The agitation and a resuspension of any sediment in the specimen in chamber 32 is aided by vanes 47 in the floor of chamber 32 (FIG. 5e).

When the machine computer system has rotated container 30 two revolutions, the machine computer system controls vertical drive servomotor 480 to lower support sleeve 405 and reseat container 30 back in rack 50.

Then support sleeve rotation drive servomotor 408 is controlled by the machine computer system to rotate container 30 to place a located and selected (or not deselected) nozzle 42 in coaxial alignment with the fixed focal point of laser system 500. The bellows assembly feature of container 30 has automatically adjusted the volume of chamber 32 since sealing to prevent any pressure differential between the interior of chamber 32 and ambient pressure. A negative intrachamber pressure relative to the ambient pressure is now induced by increasing the distance between the top and bottom of chamber 32. Vertical drive servomotor 480 is controlled to further lower support sleeve 405 and thereby collet grip head 413. With container 30 seated in rack 50, this additional movement pulls down floor plate 41a of bellows assembly 41 relative to base 40 of lower sample chamber 32 and increases the volume of lower sample chamber 32. Because chamber 32 is sealed, this increase in chamber volume reduces the intra-chamber pressure relative to ambient pressure. Vanes 47 provide structure and additional rigidity to the floor plate of bellows assembly 41, and this furnishes additional assurance that bellows assembly 41 pulls down essentially horizontally, maintaining nozzles 42 in a substantially vertical orientation and retaining the placed nozzle 42 in substantial coaxial alignment with the fixed focal point of laser system 500.

Laser power supply and electrocontroller 505 is then controlled by the machine computer system to electromechanically snap laser lens 504 into place centered in the laser beam axis. The focal point of the lens coincides with the bottom of nozzle 42 placed in coaxial alignment with the laser beam axis. The machine computer system controls the solenoid actuating laser shutter 503 to move shutter 503 out of the laser beam path and controls the laser power supply to power the laser. With the shutter open, the laser emits a beam which is focused by lens 504 onto the nozzle closure. The laser energy heats the nozzle closure and melts an opening in the closure. The opening of the nozzle closure breaches the means of maintaining the pressure differential created by the pull down of bellows assembly 41. Ambient air at higher pressure rushes upwardly into the nozzle opening and into the nozzle duct and chamber 32 to equilibrate pressure. This influx of gas and any bubbles formed in the duct by the entering air prevents immediate release of liquid from opened nozzle 42. Preferably the ratio of the pierced opening diameter to the length of the nozzle duct is maintained sufficiently small also to contribute to resistance of liquid flow from the opened nozzle.

The closure of nozzle 42 need not be at the tip of the nozzle. As shown in FIG. 4g, the closure may be located deep within the nozzle duct. This latter configuration eliminates the need for two optoelectrical sensors 340, 341 where two are used only to detect a previously truncated nozzle or nozzles. The nozzle configuration of FIG. 4g also provides advantages hereinafter described in respect to filling the aliquot receptacle.

After an exposure time of 250 to 450 milliseconds, the laser shutter solenoid is actuated and moves laser shutter 503 across the beam and the laser power source is powered down.

Then support sleeve rotation servomotor 408 is actuated by the machine computer system to rotate support sleeve and thus container 30 from alignment of opened nozzle over laser station 500 until opened nozzle 42 is disposed over the aliquot receptacle 90 at dispense station 317. At the same time support sleeve vertical drive servomotor 480 is actuated to further lower support sleeve 405 and thus collet grip head 413. This further pulls down the floor plate of bellows assembly 41, assuring that no inadvertent distance closing movement occurs between collet grip head 413 and the roof of chamber 32 that could possibly reduce volume in the primary chamber sufficiently to expel some liquid from the chamber during the rotation of opened nozzle 42 to alignment over the aliquot receptacle 90 in dispense station 317.

The machine computer system then controls tongs solenoid 464 to actuate closure of tong clamp portions 470a and 470b onto flange 91 of aliquot receptacle 90. When closure is signaled by interruption of light from optoelectric emitter to detector 475 on passage between them of flag 466 at the end of wand 465, the machine computer system then controls vertical tong drive servomotor 453 to lift tong members 460a and 460b (with tong clamp portions 470a and 470b clamped on aliquot receptacle flange 91) to a level elevating the top of flange 91 above the tip of nozzle 42.

The machine computer system then controls motor 360 to lower plate 362 to an extended position immediately above lid 35 of container 30, suitably about 1/32 of an inch. Support sleeve vertical drive servomotor 408 is then actuated to raise support sleeve 405 and thereby collet grip head 413 and thereby the floor plate of bellows assembly 41 upwardly a predetermined distance. Plate 362 assures there is no material vertical displacement of container 30 driven by collet grip head 413. The upward movement of collet grip head 413 pushes the floor plate of bellows assembly 41 upwardly toward the roof of chamber 32, reducing the volume of chamber 32. The liquid specimen in the chamber is incompressible. The extent of upward travel of collet grip head 413 is predetermined relative to the volume of liquid in the chamber to expel a predetermined volume of liquid from the chamber through the opened nozzle tip. The location of the top of flange 91 of aliquot receptacle 90 at a level above the tip of nozzle 42 assures that liquid specimen expelled from chamber 32 does not escape receptacle capture.

Optoelectric sensor pair 477a, 477b on tongs 460 sense whether the expelled liquid has filled receptacle 90 to the level sensed by sensor pair 477a, 477b. If the sensor emitter 477a light to sensor detector 477b is not interrupted, an error message is flagged to the machine computer system indicating a possible fill problem for the particular aliquot receptacle 90 and container 30.

The machine computer system then controls support sleeve rotation drive servomotor 408 to reposition the open nozzle 42 in the axis for the laser beam, controls laser power supply and electrocontroller 505 to actuate the solenoid to laser shutter 503 to move the shutter out of the laser beam path, and also controls the laser power supply to power the laser. Laser lens 504 is not placed in the path of the laser beam. With the shutter open, the laser emits a beam onto nozzle 42. The shutter opens for 250–400 milliseconds. This time the laser beam is unfocused and strikes the tip periphery of nozzle 42 as an unfocused column, melting the nozzle tip periphery. Lens shutter 503 is then closed for about 400 milliseconds and reopened. The cessation of beam energy while the shutter is closed allows the nozzle tip melt to flow across the tip opening. The second hit of energy fuses the closure shut. After about another 400 milliseconds, lens shutter 503 is then closed again.

Next the machine computer system controls the pull rod 417 solenoid to extend the solenoid plunger and push pull rod 417 back to home position, allowing laterally displaced grip head projections 413a, 413b, 413c and 413d to return to home position and release the grip of collet grip head 413 on container recess 45. Support sleeve vertical drive servomotor 480 is then controlled to lower support sleeve 405 to home level, tong vertical drive motor 453 is controlled to lower tongs 460 to home level, and tongs solenoid 464 is controlled to retract the solenoid plunger and return tong clamp members 470 to the relaxed home position leaving aliquot receptacle 90 seated in receiver tube 95.

Figure 5F:
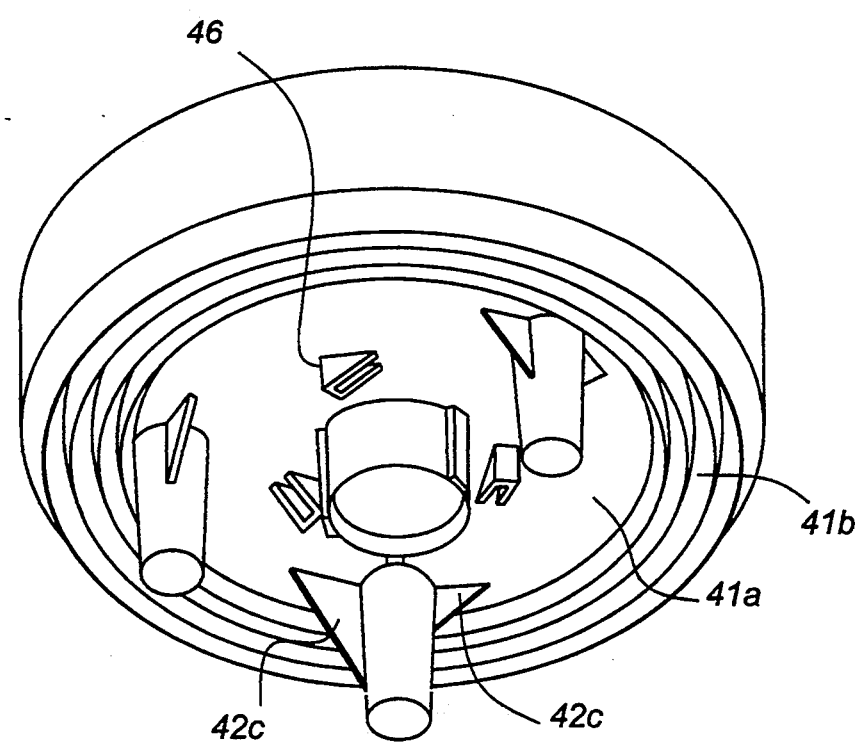
FIG. 5f is a bottom perspective view of a modified primary collection chamber bellows assembly device of FIG. 5d.

Use of a container 30 with the bellows assembly illustrated in FIG. 5f having a nozzle closure remote from the nozzle tip eliminates the need to lift aliquot receptacle 90 from receiver tube 95. This makes unnecessary aliquot receptacle manipulation system 450.

The machine computer system then indexes rack belt motor 308 to move belt 301, 302 by an amount which advances rack 50 forward one compartment. This moves the sampled specimen container from the container dispense station 317 and moves the next trailing container to container dispense station 317 for sampling. The machine computer system also controls pusher carriage drive servomotor 245 to index aliquot receptacle holder 100 forward one tube location, positioning the next trailing aliquot receptacle 90 under the second container 30 at the container dispense station.

Movement of rack 50 from dispense station 317 on track 315 slides the nib(s) adjacent the lead slot window in rack 50 into the U-channel of the one (or more) of optoelectrical sensors 318 that is (are) at the elevation accepting the particular ones of the nib(s) 80–86 adjacent the lead slot window ("1" or "5"). The particular combination of sensors triggered identifies the particular compartment of rack 50 in which the particular sampled container identified by dispense station bar code reader 330 is situated, i.e., rack position "1" or "5", "2" or "4" or "3", according to the extent of advance of the container through the dispense station.

The container manipulation and aliquot manipulation and dispense of specimen samples, and the container rack and aliquot receptacle indexing processes are repeated for the second container 30 and second aliquot receptacle, and so on, until all containers in the rack are sampled. After all containers in rack 50 have been sampled, the machine computer system controls rack belt drive motor 308 to advance rack 50 from container dispense station 317. A next trailing rack fed into entrance portal 20a trips sensor 325b and that rack is advanced on track 315 for processing as was the lead rack.

When the aliquot receptacle in an aliquot receptacle holder 100 has been filled, either from a container in a rack 50 or already with a blind or control from bind and control pump station 805a–805f, the machine computer system controls aliquot receptacle input carriage pusher drive servomotor 245 to drive pusher carriage 240 and push holder 100 from dispense station 317 along and then off track 230 onto a receiver slot on aliquot receptacle output queue belt 601. Aliquot receptacle pusher carriage drive servomotor 245 then retracts aliquot receptacle input carriage 240 to home (full retraction) position, locating aliquot receptacle input carriage pusher arm longitudinally behind the aliquot receptacle holder input feed station of the aliquot receptacle holder input queue belt.

When an aliquot receptacle holder is transferred from the fill track to the aliquot receptacle output queue belt receiver slot, optoelectrical 615 detects its presence. If aliquot receptacle holders are detected by both optoelectricals 615 and 616, aliquot receptacle output queue is assumed full and the machine is powered down or cycled to standby for off machine transfer of the aliquot receptacle holders, as described below. If only optoelectrical 615 detects an aliquot receptacle holder, it sends a signal to the machine computer system that causes it to activate appropriate controllers to energize aliquot receptacle output queue drive motor and index the belt in the direction away from the fill track one slot length.

Aliquot receptacle holders on the aliquot receptacle output queue belt are transferred off the machine by operation of aliquot receptacle holder transfer pusher carriage. The aliquot receptacle holder transfer pusher carriage mounts a support which hinges one end of an elongate member. A spring urges the member against the support at the hinge pivot joiner. At the other end of the elongate member, a finger depends. In a home position with the finger member urged against the member support, the finger aligns with the aliquot receptacle holder fill track and is of length to reach down to the fill track and contact an aliquot receptacle holder. Mounted horizontally on the machine frame between the aliquot receptacle output queue belt and the aliquot receptacle fill station is a plate having a slot formed therein at least the terminal portion of which is arcuate. The arcuate portion of the slot curves away from the fill track, as illustrated in a direction toward the forward direction of the aliquot receptacle output queue belt. The initial entrance portion of the slot preferably is parallel to the fill tract in alignment with the fill track. As aliquot receptacle holder transfer pusher carriage moves to its fully retracted position, the finger on the hinged member slides into the slot and follows the curve described by the slot. This moves the finger out of the line of travel of the aliquot receptacle holder on the aliquot receptacle fill track. When the aliquot receptacle holder transfer pusher carriage moves toward the aliquot receptacle output queue belt, the finger moves along the slot and is urged by the spring back to a home position in the line of the fill track.

Optoelectrical 615 is mounted at the end of a pivot arm pivotally connected to a support mounted to the machine frame. In a home position a spring connected to the support and the pivot arm maintains the pivot arm end and optoelectrical 615 in line with the fill track and receiver slot location for the aliquot receptacle output queue belt. A solenoid moves the pivot arm out of interference with travel of aliquot receptacle holders moving in an extension of the line of travel of the AR fill track. The optoelectrical 615 pivot arm spring returns the pivot arm to home position when the solenoid reverses.

A transfer bridge provides alignment and joiner to a receiving station, which may be an input to an automated fluid analysis machine. Optoelectrical 615 pivot arm is situated between aliquot receptacle output queue belt and the transfer bridge.

Suitably, when optoelectricals 615 and 616 signal a full aliquot receptacle output queue, the fill operations of the machine are paused to standby, and the machine computer system controls the appropriate controller to energize aliquot receptacle holder transfer pusher carriage drive servomotor and move the aliquot receptacle holder transfer pusher carriage along the aliquot receptacle holder transfer pusher carriage arm from the fully retracted position of the aliquot receptacle holder transfer pusher carriage. This moves the aliquot receptacle holder transfer pusher carriage in a direction parallel to the fill track toward the aliquot receptacle output queue belt and moves aliquot receptacle holder transfer pusher carriage pusher finger into the line of the fill track. Also, the optoelectrical 615 pivot arm solenoid is energized and moves the optoelectrical 615 pivot arm out of line of feed between the aliquot receptacle output queue receiver slot and the transfer bridge. The aliquot receptacle holder transfer pusher carriage pusher finger contacts the aliquot receptacle holder in the aliquot receptacle output queue belt receiver slot for the fill track, and pushes that aliquot receptacle holder from that slot into and through the transfer bridge to the receiver machine. An optoelectrical at the end of travel of the transfer arm signals end of transit, and the aliquot receptacle holder transfer pusher carriage drive servomotor reverses and moves the aliquot receptacle holder transfer pusher carriage back to a retro position locating the aliquot receptacle holder transfer pusher carriage pusher finger on the fill track side of the aliquot receptacle output queue belt. The machine computer system then causes the belt to reverse index one slot space and present another aliquot receptacle holder in the aliquot receptacle output queue receiver slot position. The aliquot receptacle holder transfer pusher carriage is again driven forward on the aliquot receptacle holder transfer pusher carriage arm and pusher finger pushes the aliquot receptacle holder in the receiver slot from that slot through the transfer bridge to the receiver machine, and so on, until optoelectrical 615 detects an absence of an aliquot receptacle holder in the aliquot receptacle output queue belt receiver slot.

Having described the invention conceptually and in detail equivalent structures for performing the same function in substantially the same way to obtain substantially the same result are meant to be comprised within the invention.

What is claimed is:

1. A method of transferring a sample of liquid from a sealed non-deformingly expandable container containing gas and the liquid without invasively contacting the liquid remaining inside the container, said method comprising:
    (a) non-deformingly volumetrically expanding said sealed container sufficiently to reduce pressure therein below ambient pressure outside the container,
    (b) applying heat selectively to a locus on said container to non-invasively create a hole having a diameter effective to equilibrate the pressure inside the container with said ambient pressure without loss of liquid from the container, and
    (c) non-deformingly volumetrically reducing said container to expel liquid from the container through said hole.

2. The method of claim 1 in which step (b) includes creating said hole with a laser beam.

3. The method of claim 1 in which said step (b) includes creating said hole with a heated gas stream column.

4. The method of claim 1 in which said hole has a diameter effective in said container to provide surface tension at the hole greater than the hydrostatic pressure within the enlarged container.

5. The method of claim 1 in which said locus is at a bottom portion of the container when the hole is being created.

6. The method of claim 1 in which the container includes a projection from a bottom portion thereof, said projection having a duct opening into the container and having a closure closing said duct remotely from said duct opening, and wherein said locus is at said closure.

7. A method of transferring an aqueous liquid specimen from a sealed non-deformingly expandable container containing gas and a liquid without invasively contacting liquid inside the container, such container having a bottom portion including at least one nozzle portion dependent therefrom, said nozzle having a duct opening into the container and a closure closing said duct remotely from said duct opening, said method comprising:
    (a) placing said liquid specimen container and a receptacle for the liquid specimen so that the container is in a dispense station above said receptacle,
    (b) non-deformingly volumetrically expanding said container sufficiently to reduce pressure therein below ambient pressure outside the container,
    (c) applying heat selectively to a locus on said duct closure to non-invasively create a hole in the closure having a diameter effective to equilibrate the pressure inside the container with said ambient pressure without loss of liquid from the container, and
    (d) non-deformingly reducing the volume of said container to expel liquid from the container through said hole into said receptacle.

8. The method of claim 7 wherein said said nozzle is not over said receptacle when step (c) is conducted, and further comprising locating said nozzle over said receptacle before said step (d) is conducted.

9. The method of claim 8 further comprising locating said receptacle so that the bottom of said nozzle is below the top of said receptacle.

10. The method of claim 7 further comprising, after step (d), applying heat selectively to the periphery of said locus to melt close said hole.

11. The method of claim 7 in which said container has a readable identification code and said receptacle contains a readable identification code, and wherein said method further comprises:
    reading said code of a container and said code of a receptacle, for correlating the code identification of a container from which liquid is expelled to the code identification of the receptacle into which the liquid is expelled.

12. The method of claim 11 in which said step of reading includes rotating the container past a code reader, and wherein said method further comprises:
    determining the position of said nozzle, and moving said nozzle to a position for conduct of said step of opening.

13. The method of claim 11 in which said step (a) is further characterized in that said receptacle is among a plurality of receptacles in a holder and said container is among a plurality of containers in a rack, and wherein said rack has a readable identification code, said method further comprising correlating the code identification of the rack to said code identification of each said receptacle receiving liquid from a container in said rack.

14. The method of claim 7 in which said step (a) is further characterized in that said receptacle is among a plurality of receptacles in a holder and said container is among a plurality of containers in a rack, and wherein said placing includes advancing said holder and said rack in intersecting directions to place said container in said dispense station above said receptacle, and further comprising:
    after said step (d), advancing said holder and said rack to place another container in said dispense station above another said receptacle, and
    conducting said steps (b), (c) and (d) on said other container, said receptacle in step (d) being said other receptacle.

15. The method of claim 7 further comprising:
forming an input queue of a plurality of said holders, and
feeding said holders from said input queue for advancement in said first direction.

16. The method of claim 15 in which said input queue is transverse to said first direction.

17. The method of claim 7 in which after a predetermined one of said receptacles in said holder receives liquid, said holder is advanced in said first direction from below said dispense station to an output position.

18. The method of claim 17 further comprising:
receiving a holder at said output position, and
forming an output queue of a plurality of said received holders.

19. The method of claim 18 in which said output queue is transverse to said first direction.

20. A method of transferring to a receptacle an aliquot of an aqueous liquid specimen from a sealed non-deformingly expandable container containing gas and a liquid,
said container having a bottom portion including at least one nozzle portion dependent therefrom, said nozzle having a duct opening into the container and a closure closing said duct remotely from said duct opening,
said container having a readable identification code on the exterior thereof and being one of a plurality of containers in a rack, said rack having a readable identification code and including a code structure adjacent each container for identification of the location of the container in the rack,
said receptacle having a readable identification code on the exterior thereof and being one of a plurality of receptacles in a holder,
said method comprising:
  (a) feeding a first said holder for advancement in a first direction to place a first said receptacle below a dispense station,
  (b) reading said code of said first receptacle,
  (c) reading the rack code identification, for correlating the code identification of the rack to said code identification of the receptacle in said holder
  (d) feeding a first said rack in a second direction transverse to said first direction to place said first container at said dispense station above said first receptacle,
  (e) rotating said first container past (i) a code reader and reading said code of said container, for correlating the code identification of the container at the dispense station to the code identification of said first receptacle below the dispense station, and past (ii) a nozzle detecting sensor for determining the position of a said nozzle,
  (f) determining the position of a said nozzle on said first container and rotating said container at said dispensing station to position said nozzle at a nozzle opening position,
  (g) non-deformingly volumetrically expanding said first container sufficiently to reduce pressure therein below ambient pressure outside the container,
  (h) applying heat selectively to a locus on said closure to non-invasively create a hole having a diameter effective to equilibrate the pressure inside the container with said ambient pressure without loss of liquid from the container,
  (i) rotating said first container at said dispensing station to position said nozzle above said first receptacle,
  (j) elevating said first receptacle from said holder so that the bottom of said nozzle is below the top of said receptacle,
  (k) non-deformingly reducing the volume of said first container to expel liquid from the container through said hole into said first receptacle,
  (l) lowering said first receptacle to said holder so that the bottom of said nozzle is above the top of said receptacle,
  (m) rotating said first container at said dispensing station to position said nozzle at a nozzle hole closing position,
  (n) applying heat selectively to the periphery of said locus to melt close said hole,
  (o) advancing said holder in said first direction and said rack in said second direction to place another container in said rack in said dispense station and another receptacle below said dispense station,
  (p) conducting said steps (b), (c) and (e)–(n) on said other container and other receptacle,
  (q) after predetermined receptacles in said holder receive liquid, advancing said holder in said first direction from said dispense station to an output position.

21. An apparatus for transferring a sample of liquid from a sealed non-deformingly expandable container containing gas and the liquid without invasively contacting the liquid remaining inside the container, said apparatus comprising in combination:
  (a) means for non-deformingly volumetrically expanding and constricting said sealed container to vary volume therein, upon expansion to reduce pressure therein below ambient pressure outside the container, and upon constriction to expel liquid from the container through a hole formed in said container, and
  (b) means for applying heat selectively to a locus on said container in an expanded condition to non-invasively create a hole having a diameter effective to equilibrate the pressure inside the sealed container with said ambient pressure without loss of liquid from the container and for applying heat selectively to the periphery of said locus of said container after constriction thereof to melt close said hole.

22. The apparatus of claim 21 in which said means (b) includes means for creating said hole with a laser beam.

23. The apparatus of claim 21 in which said means (b) includes means for creating said hole with a heated gas stream column.

24. The apparatus of claim 21 in which said hole has a diameter effective in said container to provide surface tension at the hole greater than the hydrostatic pressure within the container.

25. The apparatus of claim 21 in which said locus is at a bottom portion of the container when the hole is being created.

26. The apparatus of claim 21 in which the container includes a projection from a bottom portion thereof, said projection having a duct opening into the container and having a closure closing said duct remotely from said duct opening, and wherein said locus is at said closure.

27. An apparatus for transferring an aqueous liquid specimen from a sealed nondeformingly expandable container containing gas and a liquid without invasively contacting liquid inside the container, such container having a bottom portion including at least one nozzle portion dependent therefrom, said nozzle having a duct opening into the container and a closure closing said duct remotely from said duct opening, said apparatus comprising in operative combination:
 (a) means for placing said liquid specimen container and a receptacle for the liquid specimen so that the container is in a dispense position above said receptacle,
 (b) means for non-deformingly volumetrically expanding and constricting said sealed container to vary volume therein, upon expansion to reduce pressure therein below ambient pressure outside the container, and upon constriction to expel liquid from the container through a hole formed in said duct closure, and
 (c) means for applying heat selectively to a locus on said duct closure to non-invasively create a hole in the closure having a diameter effective to equilibrate the pressure inside the container with said ambient pressure without loss of liquid from the container and for applying convective heat selectively to the periphery of said locus to melt close said hole.

28. The apparatus of claim 27 further comprising means for detecting the location of said nozzle at said dispensing station for locating said nozzle over said receptacle before creating said hole therein.

29. The apparatus of claim 27 further comprising means for locating said receptacle so that the bottom of said nozzle is below the top of said receptacle.

30. The apparatus of claim 27 in which said container has a readable identification code and said receptacle contains a readable identification code, and wherein said apparatus further comprises:
 means for reading said code of a container and said code of a receptacle, for correlating the code identification of a container from which liquid is expelled to the code identification of the receptacle into which the liquid is expelled.

31. The apparatus of claim 27 further characterized in that said receptacle is among a plurality of receptacles in a holder and said container is among a plurality of containers in a rack, and wherein said means for placing includes means for advancing said holder and said rack in intersecting directions to place said container in said dispensing station below said receptacle.

32. The apparatus of claim 27 further comprising:
 means for forming an input queue of a plurality of said holders, and
 means for feeding said holders from said input queue for advancement in said first direction to said ready position.

33. The apparatus of claim 32 in which said input queue is transverse to said first direction.

34. The apparatus of claim 27 further comprising:
 means for receiving a holder at an output position at the terminus of said first direction of advance, and
 means for forming an output queue of a plurality of said received holders.

35. The apparatus of claim 34 in which said output queue is transverse to said first direction.

36. An apparatus for transferring to a receptacle an aliquot of an aqueous liquid specimen from a sealed non-deformingly expandable container containing gas and a liquid,
 said container having a bottom portion including at least one nozzle portion dependent therefrom, said nozzle having a duct opening into the container and a closure closing said duct remotely from said duct opening,
 said container having a readable identification code on the exterior thereof and k-ring one of a plurality of containers in a rack, said rack having a readable identification code and including a code structure adjacent each container for identification of the location of the container in the rack,
 said receptacle having a readable identification code on the exterior thereof and being one of a plurality of receptacles in a holder,
 said apparatus comprising in operative combination:
 (a) means for feeding a first said holder for advancement in a first direction to place a first said receptacle below a dispense station,
 (b) means for reading said code of said first receptacle,
 (c) means for reading the rack code identification to provide a signal for use for correlating the code identification of the rack to said code identification of the receptacle in said holder,
 (d) means for feeding a first said rack in a second direction transverse to said first direction to place said first container at said dispense station above said first receptacle,
 (e) means for reading said code of said first container for correlating the code identification of the container at the dispense station to the code identification of said first receptacle below the dispense station,
 (f) means for sensing and determining the position of a said container nozzle at said dispense station,
 (g) means for rotating said first container past (i) said means for reading said code of said container and past (ii) said means for sensing the position of a said nozzle, for rotating said container at said dispensing station to position said nozzle at a nozzle opening position, for rotating said first container at said dispensing station to position said nozzle above said first receptacle, and for rotating said first container at said dispensing station to position said nozzle at a nozzle hole closing position,
 (h) means for non-deformingly volumetrically expanding and constricting said sealed container to vary volume therein, upon expansion to reduce pressure therein below ambient pressure outside the container, and upon constriction to expel liquid from the container through a hole formed in said closure,
 (i) means for applying heat selectively to a locus on said closure to non-invasively create a hole in the closure having a diameter effective to equilibrate the pressure inside the theretofore sealed container with said ambient pressure without loss of liquid from the container and for applying heat selectively to the periphery of said locus to melt close said hole, and
 (j) means for elevating said first receptacle from said holder so that the bottom of said nozzle is below the top of said receptacle and for lowering said first receptacle to said holder so that the bottom of said nozzle is above the top of said receptacle.

* * * * *